(12) United States Patent
Iwasaki et al.

(10) Patent No.: US 9,335,644 B2
(45) Date of Patent: May 10, 2016

(54) ELECTRON TRANSPORT MATERIAL, ELECTROPHOTOGRAPHIC PHOTORECEPTOR, PROCESS CARTRIDGE, AND IMAGE FORMING APPARATUS

(71) Applicant: FUJI XEROX CO., LTD., Tokyo (JP)

(72) Inventors: Masahiro Iwasaki, Kanagawa (JP); Shinya Yamamoto, Kanagawa (JP); Jiro Korenaga, Kanagawa (JP); Daisuke Haruyama, Kanagawa (JP); Yukimi Kawabata, Kanagawa (JP); Keisuke Kusano, Kanagawa (JP); Kenta Shingu, Kanagawa (JP); Yoshifumi Shoji, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 14/617,263

(22) Filed: Feb. 9, 2015

(65) Prior Publication Data
US 2016/0085164 A1 Mar. 24, 2016

(30) Foreign Application Priority Data

Sep. 22, 2014 (JP) ................. 2014-192440

(51) Int. Cl.
*G03G 5/07* (2006.01)
*G03G 5/10* (2006.01)
(Continued)

(52) U.S. Cl.
CPC *G03G 5/10* (2013.01); *C07C 69/76* (2013.01); *C07C 255/41* (2013.01); *C07C 2103/18* (2013.01)

(58) Field of Classification Search
CPC ........ G03G 5/10; C07C 69/76; C07C 255/41; C07C 2103/18
See application file for complete search history.

(56) References Cited

U.S. PATENT DOCUMENTS 5,017,645 A * 5/1991 Ong ............. G03G 5/14769 524/726
2004/0096761 A1 5/2004 Lin et al.
(Continued)

FOREIGN PATENT DOCUMENTS

JP H07-287407 A 10/1995
JP H08-134019 A 5/1996
(Continued)

*Primary Examiner* — Peter Vajda
(74) *Attorney, Agent, or Firm* — Oliff PLC

(57) ABSTRACT

Provided is an electron transport material represented by formula (1):

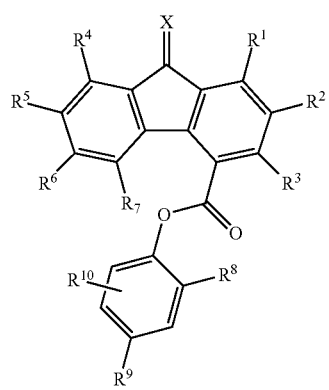

Formula (1)

wherein X represents an oxygen atom or $=C(CN)_2$; $R^1$, $R^2$, $R^3$, $R^4$, $R^5$, $R^6$, and $R^7$ each independently represent a hydrogen atom, a halogen atom, a linear or branched alkyl group, an alkoxy group, an aryl group, or an aralkyl group; $R^8$, $R^9$, and $R^{10}$ each independently represent a hydrogen atom, a halogen atom, a linear or branched alkyl group, an aralkyl group, an aryl group, $-R^{11}-O-R^{12}$, or $-R^{13}-CO-O-R^{14}$; $R^{11}$ represents a linear or branched alkylene group; $R^{12}$ represents a linear or branched alkyl group; $R^{13}$ represents a single bond or a linear or branched alkylene group; and $R^{14}$ represents a linear or branched alkyl group, an aryl group, or an aralkyl group, provided that at least two or more groups of $R^8$, $R^9$, and $R^{10}$ represent a group other than a hydrogen atom.

8 Claims, 8 Drawing Sheets

IR SPECTRUM OF EXEMPLARY COMPOUND (I-36)

(51) Int. Cl.
    *C07C 69/76*     (2006.01)
    *C07C 255/41*     (2006.01)

(56) References Cited

U.S. PATENT DOCUMENTS

| | | |
|---|---|---|
| 2004/0142260 A1 | 7/2004 | Lee et al. |
| 2005/0164106 A1 | 7/2005 | Bender et al. |
| 2006/0142444 A1 | 6/2006 | Lee et al. |
| 2007/0026331 A1 | 2/2007 | Lee et al. |

FOREIGN PATENT DOCUMENTS

| | | |
|---|---|---|
| JP | H09-43876 A | 2/1997 |
| JP | H09-265198 A | 10/1997 |
| JP | 3470160 B2 | 11/2003 |
| JP | 2004-133470 A | 4/2004 |
| JP | 2004-170984 A | 6/2004 |
| JP | 2005-121887 A | 5/2005 |
| JP | 2005-215677 A | 8/2005 |
| JP | 3697253 B2 | 9/2005 |

* cited by examiner

IR SPECTRUM OF EXEMPLARY COMPOUND (I-36)

IR SPECTRUM OF EXEMPLARY COMPOUND (I-37)

IR SPECTRUM OF EXEMPLARY COMPOUND (I-11)

IR SPECTRUM OF EXEMPLARY COMPOUND (I-12)

INFRARED ABSORPTION SPECTRUM
OF COMPARATIVE COMPOUND 1

ELECTRON TRANSPORT MATERIAL, ELECTROPHOTOGRAPHIC PHOTORECEPTOR, PROCESS CARTRIDGE, AND IMAGE FORMING APPARATUS

CROSS-REFERENCE TO RELATED APPLICATIONS

This application is based on and claims priority under 35 USC 119 from Japanese Patent Application No. 2014-192440 filed Sep. 22, 2014.

BACKGROUND

Technical Field

The present invention relates to an electron transport material, an electrophotographic photoreceptor, a process cartridge, and an image forming apparatus.

SUMMARY

According to an aspect of the invention, there is provided an electron transport material represented by the following formula (1):

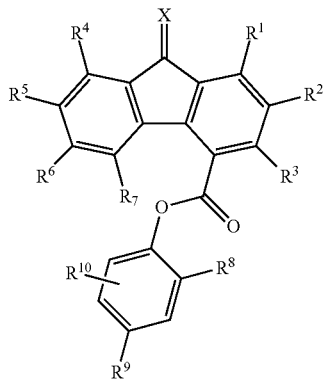

Formula (1)

wherein in the formula (1), X represents an oxygen atom or $=C(CN)_2$; $R^1$, $R^2$, $R^3$, $R^4$, $R^5$, $R^6$, and $R^7$ each independently represent a hydrogen atom, a halogen atom, a linear or branched alkyl group having 1 to 20 carbon atoms, an alkoxy group, an aryl group, or an aralkyl group; $R^8$, $R^9$, and $R^{10}$ each independently represent a hydrogen atom, a halogen atom, a linear or branched alkyl group having 1 to 20 carbon atoms, an aralkyl group, an aryl group, $-R^{11}-O-R^{12}$, or $-R^{13}-CO-O-R^{14}$; $R^{11}$ represents a linear or branched alkylene group having 1 to 10 carbon atoms; $R^{12}$ represents a linear or branched alkyl group having 1 to 10 carbon atoms; $R^{13}$ represents a single bond or a linear or branched alkylene group having 1 to 10 carbon atoms; and $R^{14}$ represents a linear or branched alkyl group having 1 to 10 carbon atoms, an aryl group, or an aralkyl group, provided that at least two or more groups of $R^8$, $R^9$, and $R^{10}$ represent a group other than a hydrogen atom.

BRIEF DESCRIPTION OF THE DRAWINGS

Exemplary embodiments of the present invention will be described in detail based on the following figures, wherein.

DETAILED DESCRIPTION

Figure 1:
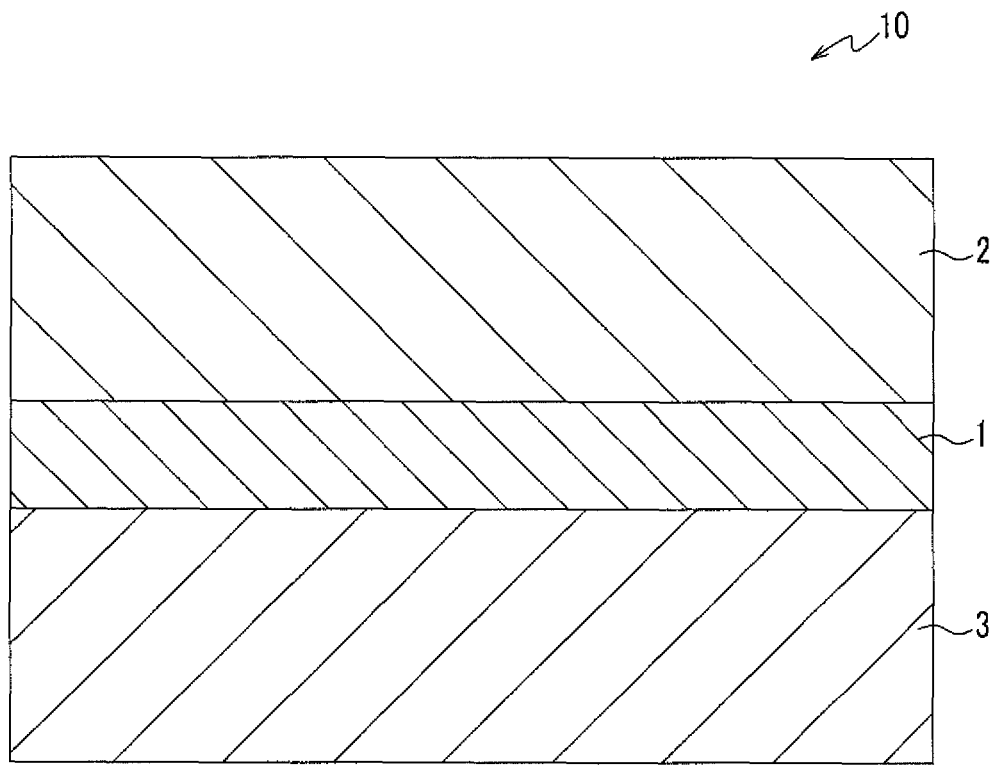
FIG. 1 is a schematic partial cross-sectional view showing an electrophotographic photoreceptor according to the present exemplary embodiment.

Hereinafter, the exemplary embodiments of the invention will be described in detail.

Electron Transport Material

The electron transport material according to the present exemplary embodiment is an electron transport material represented by the following formula (1).

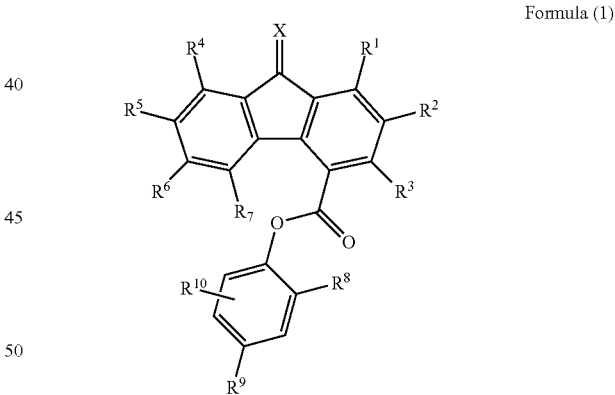

Formula (1)

In the formula (1), X represents an oxygen atom or $=C(CN)_2$. $R^1$, $R^2$, $R^3$, $R^4$, $R^5$, $R^6$, and $R^7$ each independently represent a hydrogen atom, a halogen atom, a linear or branched alkyl group having 1 to 20 carbon atoms, an alkoxy group, an aryl group, or an aralkyl group. $R^8$, $R^9$, and $R^{10}$ each independently represent a hydrogen atom, a halogen atom, a linear or branched alkyl group having 1 to 20 carbon atoms, an aralkyl group, an aryl group, $-R^{11}-O-R^{12}$, or $-R^{13}-CO-O-R^4$. $R^{11}$ represents a linear or branched alkylene group having 1 to 10 carbon atoms. $R^{12}$ represents a linear or branched alkyl group having 1 to 10 carbon atoms. $R^{13}$ represents a single bond or a linear or branched alkylene group having 1 to 10 carbon atoms. $R^{14}$ represents a linear or branched alkyl group having 1 to 10 carbon atoms, an aryl group, or an aralkyl group, provided that at least two or more groups of $R^8$, $R^9$, and $R^{10}$ represent a group other than a hydrogen atom.

As a compound having a fluorenone skeleton (hereinafter referred to as a "fluorenone derivative" in some cases), there are many compounds having a high electron transport capability but have a low compatibility with a resin. Further, for example, a fluorenone derivative having an alkoxycarbonyl group introduced into a fluorenone skeleton as a substituent for improving the compatibility with a resin has a higher compatibility with a resin, as compared with the compound which does not have a substituent, but is susceptible to an effect by a stimulus from the outside (for example, heat, an electric field, and pressure).

Examples of the effect by a stimulus from the outside include aggregation or diffusion of molecules of a fluorenone derivative in a system by a stimulus such as heat and pressure from the outside to a compound having a fluorenone derivative. Further, in the case where the molecules of a fluorenone derivative are easily aggregated or diffused in a system, it may be thought that depending on a stimulus such as heat and pressure from the outside, the distribution of fluorenone derivatives in a system is uneven.

Meanwhile, with respect to the electron transport material according to the present exemplary embodiment, even when a stimulus from the outside is received, aggregation or diffusion of the molecules over time hardly occurs in a system. The reason for this is not clear, but it is presumed that by introducing a phenyl group having two or more specific substituents through an ester bond, the motion of the ester group at the 4-position in the fluorenone skeleton is confined by steric hindrance, and thus, a change in the molecular structure by the stimulus from the outside hardly occurs. Specifically, for example, it may also be thought that by steric hindrance of a substituent, a change in the physical structure of the phenyl group such as rotation is prevented, and in addition, a change in the chemical molecular structure such as hydrolysis of an ester group at a high temperature and a high humidity is also prevented.

As a result, for example, it is thought that in a resin layer including the electron transport material according to the present exemplary embodiment, even when a stimulus occurs from the outside, the molecular motion of the electron transport material in the resin layer is prevented, and thus, the morphological change of the film hardly occurs.

Therefore, the electrophotographic photoreceptor using the electron transport material according to the present exemplary embodiment, even when the image formation is repeated, blurring of an image due to a change in the film quality of the photosensitive layer or a change of the physical properties of the photosensitive layer surface hardly occurs. In addition, in the exemplary embodiment, even when the image formation is repeated, the film quality is hardly changed and the charge maintenance is good.

Furthermore, the electron transport material according to the present exemplary embodiment has a phenyl group having two or more substituents incorporated thereinto, and therefore, it has a high melting point as well as high compatibility with a resin, as compared with a case where an electron transport material has a phenyl group having no substituent or a phenyl group having only one substituent incorporated thereinto.

That is, by the electron transport material according to the present exemplary embodiment, improvement of the compatibility with a resin and prevention of the morphological change of the film as well as an electron transport capability are accomplished. Further, by using an electrophotographic photoreceptor in which a resin layer including the electron transport material according to the present exemplary embodiment is used as a photosensitive layer, blurring of an image hardly occurs, and the charge maintenance becomes better.

Hereinafter, the electron transport material according to the present exemplary embodiment will be described in detail.

In the formula (1), examples of the halogen atom represented by $R^1$ to $R^7$ include a fluorine atom, a chlorine atom, a bromine atom, and an iodine atom, and from the viewpoints of the chemical stability, a fluorine atom and a chlorine atom are preferable.

In the formula (1), examples of the linear or branched alkyl group having 1 to 20 carbon atoms represented by $R^1$ to $R^7$ include a methyl group, an ethyl group, an n-propyl group, an n-butyl group, an n-pentyl group, an n-hexyl group, an n-heptyl group, an n-octyl group, an n-nonyl group, an n-decyl group, an isopropyl group, an isobutyl group, a sec-butyl group, a tert-butyl group, an isopentyl group, a neopentyl group, a tert-pentyl group, an isohexyl group, a sec-hexyl group, a tert-hexyl group, an isoheptyl group, a sec-heptyl group, a tert-heptyl group, an isooctyl group, a sec-octyl group, a tert-octyl group, an isononyl group, a sec-nonyl group, a tert-nonyl group, an isodecyl group, a sec-decyl group, and a tert-decyl group. In the formula (1), the number of carbon atoms of the alkyl group represented by $R^1$ to $R^7$ is preferably from 1 to 4, and more preferably from 1 to 3, from the viewpoints of prevention of the molecular motion in a layer and compatibility.

In the formula (1), examples of the alkoxy group represented by $R^1$ to $R^7$ include a linear or branched alkoxy group having 1 to 4 carbon atoms, and specific examples thereof include a methoxy group, an ethoxy group, a propoxy group, and a butoxy group. In the formula (1), the number of carbon atoms of the alkoxy group represented by $R^1$ to $R^7$ is preferably from 1 to 3, from the viewpoints of prevention of the morphological change of the film.

In the formula (1), the aryl group represented by $R^1$ to $R^7$ may or may not have a substituent, and examples thereof include substituted or unsubstituted phenyl groups. Examples of the substituent contained in the aryl group include an alkyl group having 1 to 10 carbon atoms, an alkoxy group, and a halogen atom. Specific examples of the aryl group include a phenyl group, a methylphenyl group (tolyl group), a dimethylphenyl group, and an ethylphenyl group.

In the formula (1), examples of the aralkyl group represented by $R^1$ to $R^7$ include a group represented by —$R^{15}$—$Ar^{16}$, provided that $R^{15}$ represents an alkylene group and $Ar^{16}$ represents a substituted or unsubstituted aryl group.

Examples of the alkylene group represented by $R^{15}$ include a linear or branched alkylene group having 1 to 12 carbon atoms, and specific examples thereof include a methylene group, an ethylene group, an n-propylene group, an isopropylene group, an n-butylene group, an isobutylene group, a sec-butylene group, a tert-butylene group, an n-pentylene group, an isopentylene group, a neopentylene group, and a tert-pentylene group. The number of carbon atoms of the alkylene group represented by $R^{15}$ is preferably from 1 to 10, and more preferably from 1 to 6, from the viewpoints of compatibility and solubility.

Examples of the substituted or unsubstituted aryl group represented by $Ar^{16}$ include the same groups as set forth above with respect to the aryl group represented by $R^1$ to $R^7$ in the formula (1), and examples of the substituent that the aryl group has also include the same groups as set forth above.

In the formula (1), specific examples of the aralkyl group represented by $R^1$ to $R^7$ include a benzyl group, a methylbenzyl group, a dimethylbenzyl group, a phenylethyl group, a methylphenylethyl group, a phenylpropyl group, and a phenylbutyl group.

$R^1$ to $R^7$ in the formula (1) are each independently preferably a hydrogen atom, a halogen atom, a linear alkyl group having 1 to 10 carbon atoms, or a linear alkoxy group having 1 to 10 carbon atoms, and more preferably a hydrogen atom, from the viewpoints of a high electron transport capability and prevention of the morphological change of the film.

Furthermore, examples of a combination of $R^1$ to $R^7$ in the formula (1) include a combination in which $R^1$ to $R^7$ are all hydrogen atoms, a combination in which six groups out of $R^1$ to $R^7$ are hydrogen atoms and the one group is a group other than a hydrogen atom, and a combination in which five groups out of $R^1$ to $R^7$ are hydrogen atoms and the two groups are groups other than a hydrogen atom.

In the formula (1), examples of the halogen atom represented by $R^8$ to $R^{10}$ include a fluorine atom, a chlorine atom, a bromine atom, and an iodine atom, and from the viewpoints of the chemical stability, a fluorine atom and a chlorine atom are preferable.

In the formula (1), examples of the linear alkyl group with respect to the linear or branched alkyl group having 1 to 20 carbon atoms represented by $R^8$ to $R^{10}$ include a methyl group, an ethyl group, an n-propyl group, an n-butyl group, an n-pentyl group, an n-hexyl group, an n-heptyl group, an n-octyl group, an n-nonyl group, and an n-decyl group.

In the formula (1), examples of the branched alkyl group with respect to the linear or branched alkyl group having 1 to 20 carbon atoms represented by $R^8$ to $R^{10}$ include an isopropyl group, an isobutyl group, a sec-butyl group, a tert-butyl group, an isopentyl group, a neopentyl group, a tert-pentyl group, an isohexyl group, a sec-hexyl group, a tert-hexyl group, an isoheptyl group, a sec-heptyl group, a tert-heptyl group, an isooctyl group, a sec-octyl group, a tert-octyl group, an isononyl group, a sec-nonyl group, a tert-nonyl group, an isodecyl group, a sec-decyl group, and a tert-decyl group.

In the formula (1), the number of carbon atoms of the linear alkyl group represented by $R^8$ to $R^{10}$ is preferably from 1 to 10, and more preferably from 1 to 6, from the viewpoints of improvement of compatibility with a resin and prevention of film morphology. Further, in the formula (1), the number of carbon atoms of the branched alkyl group represented by $R^8$ to $R^{10}$ is preferably from 3 to 10, and more preferably from 3 to 6, from the viewpoints of improvement of the compatibility with a resin.

In the formula (1), examples of the aralkyl group represented by $R^8$ to $R^{10}$ include a group represented by —$R^{17}$—$Ar^{18}$, provided that $R^{17}$ represents an alkylene group and $Ar^{18}$ represents a substituted or unsubstituted aryl group.

Examples of the alkylene group represented by $R^{17}$ include the same groups as set forth above with respect to $R^{15}$ of the group represented by —$R^{15}$—$Ar^{16}$. The number of carbon atoms of the alkylene group represented by $R^{17}$ is preferably from 1 to 10, and preferably from 1 to 6, from the viewpoints of prevention of the morphological change of the film.

Examples of the aryl group represented by $Ar^{18}$ include the same groups as set forth above with respect to $Ar^{16}$ of the group represented by —$R^{15}$—$Ar^{16}$.

In the formula (1), specific examples of the aralkyl group represented by $R^8$ to $R^{10}$ include the specific examples of the aralkyl group represented by $R^1$ to $R^7$.

In the formula (1), specific examples of the aryl group represented by $R^8$ to $R^{10}$ include the specific examples of the aryl group represented by $R^1$ to $R^7$.

In the formula (1), in a group represented by —$R^{11}$—O—$R^{12}$ represented by $R^8$ to $R^{10}$, $R^{11}$ represents a linear or branched alkylene group having 1 to 10 carbon atoms, and $R^{12}$ represents a linear or branched alkyl group having 1 to 10 carbon atoms.

Examples of the linear or branched alkylene group having 1 to 10 carbon atoms represented by $R^{11}$ include the same groups as set forth above with respect to the specific examples of the alkylene group represented by $R^{15}$ in the group represented by —$R^{15}$—$Ar^{16}$. The number of carbon atoms of the alkylene group represented by $R^{11}$ is preferably from 1 to 10. Further, the alkylene group represented by $R^{11}$ is preferably a branched alkylene group having 1 to 10 carbon atoms.

Examples of the linear or branched alkyl group having 1 to 10 carbon atoms represented by $R^{12}$ include the same groups as set forth above with respect to the specific examples of the alkyl group represented by $R^8$ to $R^{10}$. The number of carbon atoms of the alkyl group represented by $R^{12}$ is preferably from 1 to 10.

As the group represented by —$R^{11}$—O—$R^{12}$, which is represented by $R^8$ to $R^{10}$, above all, a methoxymethyl group, an ethoxymethyl group, or a phenoxymethyl group is preferable.

In the formula (1), in the group represented by —$R^{13}$—CO—O—$R^{14}$, which is represented by $R^8$ to $R^{10}$, $R^{13}$ represents a single bond or a linear or branched alkylene group having 1 to 10 carbon atoms, and $R^{14}$ represents a linear or branched alkyl group having 1 to 10 carbon atoms, an aryl group, or an aralkyl group.

Examples of the linear or branched alkylene group having 1 to 10 carbon atoms represented by $R^{13}$ include the same groups as set forth above with respect to the specific examples of the alkylene group represented by $R^{15}$ of the group represented by —$R^{15}$—$Ar^{16}$. The number of carbon atoms of the alkylene group represented by $R^{13}$ is preferably from 1 to 10. Further, the alkylene group represented by $R^{13}$ is preferably a branched alkylene group having 1 to 6 carbon atoms.

Examples of the linear or branched alkyl group having 1 to 10 carbon atoms represented by $R^{14}$ include the same groups as set forth above with respect to the specific examples of the alkyl group represented by $R^8$ to $R^{10}$. The number of carbon atoms of the alkyl group represented by $R^{14}$ is preferably from 1 to 10. Further, the alkyl group represented by $R^{14}$ is preferably a branched alkyl group having 1 to 10 carbon atoms.

Examples of the aryl group represented by $R^{14}$ include the same groups as set forth above with respect to the specific examples of the aryl group represented by $Ar^{16}$ of the group represented by —$R^{15}$—$Ar^{16}$. The substituents introduced to the aryl group, the preferable groups, and the like are the same as for the aryl group represented by $Ar^{16}$ of the group represented by —$R^5$—$Ar^6$.

Examples of the aralkyl group represented by $R^{14}$ include the same groups as set forth above with respect to the specific examples of the aralkyl group represented by $R^8$ to $R^{10}$. The preferable groups are the same as for the aralkyl group represented by $R^8$ to $R^{10}$.

As the group represented by —$R^{13}$—CO—O—$R^{14}$, which is represented by $R^8$ to $R^{10}$, above all, a methoxycarbonylmethyl and an ethoxycarbonylmethyl group are preferable.

The binding position of $R^{10}$ in the formula (1) may be any of the 3-position, the 5-position, and the 6-position as long as it is a position other than the 2-position to which $R^8$ is bonded and the 4-position to which $R^9$ is bonded, and the 6-position is more preferable.

Above all, $R^8$ to $R^{10}$ in the formula (1) are each independently preferably a hydrogen atom, a chlorine atom, a linear alkyl group having 1 to 10 carbon atoms, a branched alkyl group having 3 to 10 carbon atoms, the aralkyl group represented by —$R^{17}$—$Ar^{18}$ ($R^{17}$ represents a branched alkylene group having 3 to 10 carbon atoms and $Ar^{18}$ represents a substituted or unsubstituted phenyl group), —$R^{11}$—O—$R^{12}$ ($R^{11}$ represents an alkylene group having 1 to 10 carbon atoms, and $R^{12}$ represents an alkyl group having 1 to 10 carbon atoms), —$R^{13}$—CO—O—$R^{14}$ ($R^{13}$ represents a single bond or an alkylene group having 1 to 10 carbon atoms, and $R^{14}$ represents a linear or branched alkyl group having 1 to 10 carbon atoms or an aralkyl group); and more preferably a hydrogen atom, a linear alkyl group having 1 to 10 carbon atoms, or a branched alkyl group having 3 to 10 carbon atoms.

$R^8$ to $R^{10}$ in the formula (1) may be any groups such that two or more groups of these groups are groups other than a hydrogen atom, but it is preferable that one or more groups of $R^8$ to $R^{10}$ is each an organic group having 1 or more carbon atoms (that is, an alkyl group, an aralkyl group, an aryl group, —$R^1$—O—$R^{12}$, or —$R^{13}$—CO—O—$R^4$), and it is more preferable that two or more groups of $R^8$ to $R^{10}$ is each an organic group having 1 or more carbon atoms.

Furthermore, it is preferable that $R^8$ and $R^9$ in the formula (1) are groups other than a hydrogen atom ($R^{10}$ is a hydrogen atom or a group other than a hydrogen atom), and it is more preferable that $R^{10}$ is a hydrogen atom, and $R^8$ and $R^9$ are a group other than a hydrogen atom.

The electron transport material represented by the formula (1) is preferably the electron transport material, in which $R^1$ to $R^7$ each independently represent a hydrogen atom, a halogen atom, or an alkyl group, $R^8$ and $R^9$ represent a linear or branched alkyl group having 1 to 10 carbon atoms, or an aralkyl group, and $R^{10}$ is a hydrogen atom; in particular, in which $R^1$ to $R^7$ each independently represent a hydrogen atom, a halogen atom, or an alkyl group having 1 to 10 carbon atoms, further, $R^8$ and $R^9$ are both a branched alkyl group having 3 to 10 carbon atoms or an aralkyl group represented by —$R^7$—$Ar^8$ ($R^{17}$ is a branched alkylene group having 3 to 10 carbon atoms and $Ar^{18}$ is an unsubstituted phenyl group), and $R^{10}$ represents a hydrogen atom, from the viewpoints of improvement of compatibility with a resin and prevention of film morphology.

Hereinafter, the exemplary compounds of the electron transport material represented by the formula (1) are shown, but the invention is not limited thereto.

Furthermore, the "o-position" as the "position of $R^{10}$" in the Tables below denotes that $R^{10}$ binds at the 6-position of a benzene ring, and the "m-position" as the "position of $R^{10}$" denotes that $R^{10}$ binds at the 5-position of a benzene ring.

| Exemplary Compound | X | $R^1$ | $R^2$ | $R^3$ | $R^4$ | $R^5$ | $R^6$ | $R^7$ | $R^8$ |
|---|---|---|---|---|---|---|---|---|---|
| 1-1 | =C(CN)$_2$ | —H | —H | —H | —H | —H | —H | —H | —CH$_3$ |
| 1-2 | =C(CN)$_2$ | —H | —H | —H | —H | —H | —H | —H | —CH$_3$ |
| 1-3 | =C(CN)$_2$ | —H | —H | —H | —H | —H | —H | —H | —CH$_3$ |
| 1-4 | =C(CN)$_2$ | —H | —H | —H | —H | —H | —H | —H | —CH$_3$ |
| 1-5 | =C(CN)$_2$ | —H | —H | —H | —H | —H | —H | —H | —CH$_2$OCH$_3$ |
| 1-6 | =C(CN)$_2$ | —H | —H | —H | —H | —H | —H | —H | —CH(CH$_3$)$_2$ |
| 1-7 | =C(CN)$_2$ | —H | —H | —H | —H | —H | —H | —H | —CH(CH$_3$)$_2$ |
| 1-8 | =C(CN)$_2$ | —H | —H | —H | —H | —H | —H | —H | —CH$_3$ |
| 1-9 | =C(CN)$_2$ | —H | —H | —H | —H | —H | —H | —H | -t-C$_4$H$_9$ |
| 1-10 | =C(CN)$_2$ | —H | —H | —H | —H | —H | —H | —H | -t-C$_4$H$_9$ |
| 1-11 | =C(CN)$_2$ | —H | —H | —H | —H | —H | —H | —H | —C(CH$_3$)$_2$CH$_2$CH$_3$ |
| 1-12 | =C(CN)$_2$ | —H | —H | —H | —H | —H | —H | —H | 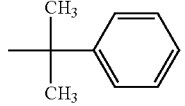 |
| 1-13 | =C(CN)$_2$ | —H | —H | —H | —H | —H | —H | —H | -t-C$_4$H$_9$ |
| 1-14 | =C(CN)$_2$ | —H | —H | —H | —H | —H | —H | —H | -t-C$_4$H$_9$ |
| 1-15 | =C(CN)$_2$ | —H | —H | —H | —H | —H | —H | —H | -t-C$_4$H$_9$ |
| 1-16 | =C(CN)$_2$ | —H | —H | —H | —H | —H | —H | —H | -t-C$_4$H$_9$ |
| 1-17 | =C(CN)$_2$ | —H | —H | —H | —H | —H | —H | —H | -t-C$_4$H$_9$ |
| 1-18 | =C(CN)$_2$ | —H | —H | —H | —H | —H | —H | —H | -t-C$_4$H$_9$ |
| 1-19 | =C(CN)$_2$ | —H | —H | —H | —H | —H | —H | —H | -t-C$_4$H$_9$ |
| 1-20 | =C(CN)$_2$ | —H | —H | —H | —H | —H | —H | —H | -t-C$_4$H$_9$ |
| 1-21 | =C(CN)$_2$ | —H | Cl | —H | —H | Cl | —H | —H | —C(CH$_3$)$_2$CH$_2$CH$_3$ |
| 1-22 | =C(CN)$_2$ | —H | Cl | —H | —H | Cl | —H | —H | -n-C$_4$H$_9$ |
| 1-23 | =C(CN)$_2$ | —H | —CH$_3$ | —H | —H | —H | —H | —H | —Cl |
| 1-24 | =C(CN)$_2$ | —H | —OCH$_3$ | —H | —H | —H | —H | —H | -n-C$_9$H$_{19}$ |
| 1-25 | =C(CN)$_2$ | —OCH$_3$ | —H | —H | —H | —H | —H | —H | —CH$_2$OCH$_3$ |
| 1-26 | =O | —H | —H | —H | —H | —H | —H | —H | —CH$_3$ |
| 1-27 | =O | —H | —H | —H | —H | —H | —H | —H | —CH$_3$ |
| 1-28 | =O | —H | —H | —H | —H | —H | —H | —H | —CH$_3$ |
| 1-29 | =O | —H | —H | —H | —H | —H | —H | —H | —CH$_3$ |
| 1-30 | =O | —H | —H | —H | —H | —H | —H | —H | —CH$_2$OCH$_3$ |
| 1-31 | =O | —H | —H | —H | —H | —H | —H | —H | —CH(CH$_3$)$_2$ |
| 1-32 | =O | —H | —H | —H | —H | —H | —H | —H | —CH(CH$_3$)$_2$ |
| 1-33 | =O | —H | —H | —H | —H | —H | —H | —H | —CH$_3$ |
| 1-34 | =O | —H | —H | —H | —H | —H | —H | —H | -t-C$_4$H$_9$ |
| 1-35 | =O | —H | —H | —H | —H | —H | —H | —H | -t-C$_4$H$_9$ |
| 1-36 | =O | —H | —H | —H | —H | —H | —H | —H | —C(CH$_3$)$_2$CH$_2$CH$_3$ |
| 1-37 | =O | —H | —H | —H | —H | —H | —H | —H | 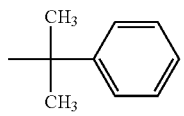 |

-continued

| | | | | | | | | | |
|---|---|---|---|---|---|---|---|---|---|
| 1-38 | =O | —H | —H | —H | —H | —H | —H | —H | -t-C$_4$H$_9$ |
| 1-39 | =O | —H | —H | —H | —H | —H | —H | —H | -t-C$_4$H$_9$ |
| 1-40 | =O | —H | —H | —H | —H | —H | —H | —H | -t-C$_4$H$_9$ |
| 1-41 | =O | —H | —H | —H | —H | —H | —H | —H | -t-C$_4$H$_9$ |
| 1-42 | =O | —H | —H | —H | —H | —H | —H | —H | -t-C$_4$H$_9$ |
| 1-43 | =O | —H | —H | —H | —H | —H | —H | —H | -t-C$_4$H$_9$ |
| 1-44 | =O | —H | —H | —H | —H | —H | —H | —H | -t-C$_4$H$_9$ |
| 1-45 | =O | —H | —H | —H | —H | —H | —H | —H | -t-C$_4$H$_9$ |
| 1-46 | =O | —H | Cl | —H | —H | Cl | —H | —H | —C(CH$_3$)$_2$CH$_2$CH$_3$ |
| 1-47 | =O | —H | Cl | —H | —H | Cl | —H | —H | -n-C$_4$H$_9$ |
| 1-48 | =O | —H | —CH$_3$ | —H | —H | —H | —H | —H | —Cl |
| 1-49 | =O | —H | —OCH$_3$ | —H | —H | —H | —H | —H | -n-C$_9$H$_{19}$ |
| 1-50 | =O | —OCH$_3$ | —H | —H | —H | —H | —H | —H | —CH$_2$OCH$_3$ |

| Exemplary Compound | R$^9$ | position of R$^{10}$ | R$^{10}$ |
|---|---|---|---|
| 1-1 | —CH$_3$ | — | —H |
| 1-2 | —CH$_3$ | o-position | —CH$_3$ |
| 1-3 | —CH$_3$ | m-position | —CH$_3$ |
| 1-4 | —C$_2$H$_5$ | — | —H |
| 1-5 | -t-C$_4$H$_9$ | o-position | —CH$_2$OCH$_3$ |
| 1-6 | —CH$_3$ | o-position | —CH(CH$_3$)$_2$ |
| 1-7 | -t-C$_4$H$_9$ | o-position | —CH(CH$_3$)$_2$ |
| 1-8 | -n-C$_6$H$_{13}$ | — | —H |
| 1-9 | —C$_2$H$_5$ | o-position | -t-C$_4$H$_9$ |
| 1-10 | -t-C$_4$H$_9$ | — | —H |
| 1-11 | —C(CH$_3$)$_2$CH$_2$CH$_3$ | — | —H |
| 1-12 | 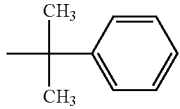 | — | —H |
| 1-13 | —CH$_2$CH$_2$CO$_2$CH$_3$ | o-position | -t-C$_4$H$_9$ |
| 1-14 | —CH$_2$CH$_2$CO$_2$CH$_2$CH$_3$ | o-position | -t-C$_4$H$_9$ |
| 1-15 | —CH$_2$CH$_2$CO$_2$CH$_2$CH$_2$CH$_3$ | o-position | -t-C$_4$H$_9$ |
| 1-16 | —CH$_2$CH$_2$CO$_2$-nC$_6$H$_{13}$ | o-position | -t-C$_4$H$_9$ |
| 1-17 | —CH$_2$CH$_2$CO$_2$-nC$_8$H$_{17}$ | o-position | -t-C$_4$H$_9$ |
| 1-18 | —CH$_2$CH$_2$CO$_2$-isoC$_8$H$_{17}$ | o-position | -t-C$_4$H$_9$ |
| 1-19 | 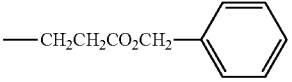 | o-position | -t-C$_4$H$_9$ |
| 1-20 | —CO$_2$-isoC$_8$H$_{17}$ | o-position | -t-C$_4$H$_9$ |
| 1-21 | —C(CH$_3$)$_2$CH$_2$CH$_3$ | — | —H |
| 1-22 | -n-C$_4$H$_9$ | — | —H |
| 1-23 | —CO$_2$-isoC$_8$H$_{17}$ | — | —H |
| 1-24 | —CO$_2$-isoC$_8$H$_{17}$ | — | —H |
| 1-25 | —CO$_2$-isoC$_8$H$_{17}$ | — | —H |
| 1-26 | —CH$_3$ | — | —H |
| 1-27 | —CH$_3$ | o-position | —CH$_3$ |
| 1-28 | —CH$_3$ | m-position | —CH$_3$ |
| 1-29 | —C$_2$H$_5$ | — | —H |
| 1-30 | -t-C$_4$H$_9$ | o-position | —CH$_2$OCH$_3$ |
| 1-31 | —CH$_3$ | o-position | —CH(CH$_3$)$_2$ |
| 1-32 | -t-C$_4$H$_9$ | o-position | —CH(CH$_3$)$_2$ |
| 1-33 | -n-C$_6$H$_{13}$ | — | —H |
| 1-34 | —C$_2$H$_5$ | o-position | -t-C$_4$H$_9$ |
| 1-35 | -t-C$_4$H$_9$ | — | —H |
| 1-36 | —C(CH$_3$)$_2$CH$_2$CH$_3$ | — | —H |
| 1-37 | 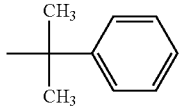 | — | —H |
| 1-38 | —CH$_2$CH$_2$CO$_2$CH$_3$ | o-position | -t-C$_4$H$_9$ |
| 1-39 | —CH$_2$CH$_2$CO$_2$CH$_2$CH$_3$ | o-position | -t-C$_4$H$_9$ |
| 1-40 | —CH$_2$CH$_2$CO$_2$CH$_2$CH$_2$CH$_3$ | o-position | -t-C$_4$H$_9$ |
| 1-41 | —CH$_2$CH$_2$CO$_2$-nC$_6$H$_{13}$ | o-position | -t-C$_4$H$_9$ |
| 1-42 | —CH$_2$CH$_2$CO$_2$-nC$_8$H$_{17}$ | o-position | -t-C$_4$H$_9$ |
| 1-43 | —CH$_2$CH$_2$CO$_2$-isoC$_8$H$_{17}$ | o-position | -t-C$_4$H$_9$ |

-continued

| | | | |
|---|---|---|---|
| 1-44 | —CH$_2$CH$_2$CO$_2$CH$_2$—  | o-position | -t-C$_4$H$_9$ |
| 1-45 | —CO$_2$-isoC$_8$H$_{17}$ | o-position | -t-C$_4$H$_9$ |
| 1-46 | —C(CH$_3$)$_2$CH$_2$CH$_3$ | — | —H |
| 1-47 | -n-C$_4$H$_9$ | — | —H |
| 1-48 | —CO$_2$-isoC$_8$H$_{17}$ | — | —H |
| 1-49 | —CO$_2$-isoC$_8$H$_{17}$ | — | —H |
| 1-50 | —CO$_2$-isoC$_8$H$_{17}$ | — | —H |

Exemplary compound, Position of R$^{10}$, o-Position, m-Position, o-Position, o-Position, o-Position, o-Position, o-Position, o-Position, o-Position, o-Position, o-Position, o-Position, o-Position, o-Position Hereinbelow, a method for preparing the electron transport material according to the present exemplary embodiment will be described.

The electron transport material represented by the formula (1) is synthesized by a known method.

By way of an example, a method for synthesizing a compound in which X is an oxygen atom or =C(CN)$_2$, R$^1$ to R$^7$ are all hydrogen atoms, R$^8$ and R$^9$ are each a methyl group, and R$^{10}$ is a hydrogen atom in the electron transport material represented by the formula (1) will be described below, but the invention is not limited thereto.

The compound in which X is an oxygen atom in the electron transport material represented by the formula (1) is obtained, for example, through the reactions of the following routes (1) and (2). Further, the compound in which X is =C(CN)$_2$ in the electron transport material represented by the formula (1) is obtained, for example, through reactions of the following routes (1) to (3).

Route 1): 9-Fluorenone-4-carboxylic acid is reacted with thionyl chloride to afford an acid chloride.

Route 2): By reacting the obtained acid chloride with a phenol derivative (for example, 2,4-xylenol) in the presence of a base catalyst (for example, pyridine, piperidine, and triethylamine) to obtain the compound of the formula (1) in which X is an oxygen atom.

Route 3) By adding malonitrile to the compound of the formula (1) in which X is an oxygen atom and reacting them with each other in the presence of the same base catalyst as in the route 2) to obtain the compound of the formula (1) in which X is a dicyanomethylene group (=C(CN)$_2$).

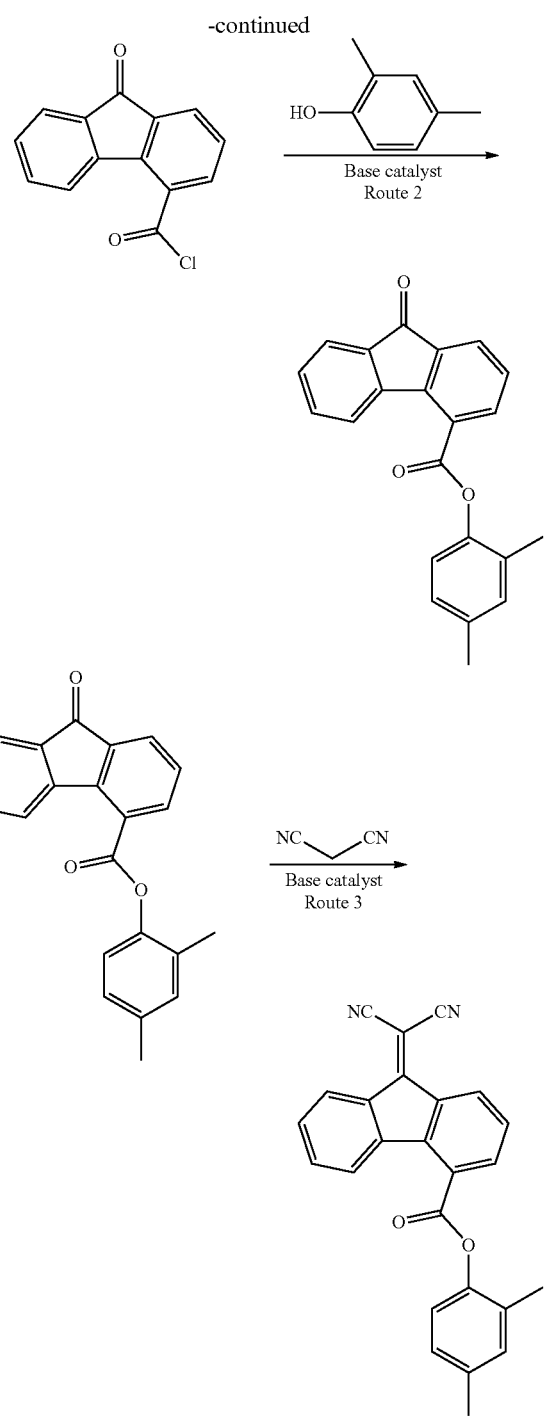

The electron transport material according to the present exemplary embodiment has a high electron transport capability and a high compatibility with a resin, and hardly causes aggregation or diffusion of the molecules in a system, and therefore, it hardly causes a morphological change in a layer. The electron transport material according to the present exemplary embodiment is suitable for, for example, a photosensitive layer of an electrophotographic photoreceptor (in particular, a single layer type photoreceptor) as described later.

Electrophotographic Photoreceptor

The electrophotographic photoreceptor according to the present exemplary embodiment has a conductive substrate and a photosensitive layer provided on the conductive substrate, in which the photosensitive layer includes an electron transport material represented by the formula (1) (hereinafter referred to as a "specific electron transport material" in some cases).

Here, the photosensitive layer may be a function integration type photosensitive layer (single layer type photosensitive layer) having both a charge transport capability and a charge generating capability, and may be a function separation type photosensitive layer including a charge transport layer and a charge generating layer. Further, in the function separation type photosensitive layer, the specific electron transport material is included in the charge transport layer.

Hereinafter, as an example, a positively charged organic photoreceptor (hereinafter simply referred to as a "photoreceptor" or a "single layer type photoreceptor" in some cases) having a single layer type photosensitive layer on a conductive substrate will be described in detail with reference to the drawings.

FIG. 1 schematically shows a cross-sectional view of a part of the electrophotographic photoreceptor 10 according to the present exemplary embodiment.

The electrophotographic photoreceptor 10 shown in FIG. 1 includes a conductive substrate 3, and has a structure in which an undercoat layer 1 and a single layer type photosensitive layer 2 are provided in this order on the conductive substrate 3.

Further, the undercoat layer 1 is a layer which is provided, as desired. That is, the single layer type photosensitive layer 2 may be provided directly or through the undercoat layer 1 on the conductive substrate 3.

Further, other layers may be provided, as necessary. Specifically, for example, a protective layer may be provided on a single layer type photosensitive layer 2, as desired.

Hereinafter, each of the layers of the electrophotographic photoreceptor according to the present exemplary embodiment will be described in detail. Further, the explanations of the symbols are omitted.

Conductive Substrate

Examples of the conductive substrate include metal plates, metal drums, and metal belts containing a metal (such as aluminum, copper, zinc, chromium, nickel, molybdenum, vanadium, indium, gold, and platinum), and alloys thereof (such as stainless steel). Further, other examples of the conductive substrate include papers, resin films, and belts which are coated, deposited, or laminated with a conductive compound (such as a conductive polymer and indium oxide), a metal (such as aluminum, palladium, and gold), or alloys thereof. The term "conductive" means that the volume resistivity is less than $10^{13}$ Ωcm.

When the electrophotographic photoreceptor is used in a laser printer, the surface of the conductive substrate is preferably roughened so as to have a centerline average roughness (Ra) of 0.04 μm to 0.5 μm sequentially to prevent interference fringes which are formed when irradiated with laser light.

Further, when an incoherent light is used as a light source, surface roughening for preventing interference fringes is not particularly necessary, but occurrence of defects due to the irregularities on the surface of the conductive substrate is prevented, which is thus suitable for achieving a longer service life.

Examples of the method for surface roughening include wet honing in which an abrasive suspended in water is blown onto a support, centerless grinding in which a support is continuously ground by pressing a conductive substrate onto a rotating grind stone, and anodic oxidation treatment.

Other examples of the method for surface roughening include a method for surface roughening by forming a layer of a resin in which conductive or semiconductive particles are dispersed in the resin so that the surface roughening is achieved by forming a layer on the surface of a conductive substrate, while not roughening the surface of the conductive substrate.

In the surface roughening treatment by anodic oxidation, an oxide film is formed on the surface of a conductive substrate by anodic oxidation in which a metal (for example, aluminum) conductive substrate as an anode is anodized in an electrolyte solution. Examples of the electrolyte solution include a sulfuric acid solution and an oxalic acid solution. However, the porous anodic oxide film formed by anodic oxidation as it is chemically active, easily contaminated and has a large resistance variation depending on the environment. Therefore, it is preferable to conduct a sealing treatment in which for a porous anodic oxide film, fine pores of the oxide film are sealed by cubical expansion caused by a hydration in pressurized water vapor or boiled water (to which a metallic salt such as a nickel salt may be added) to transform the anodic oxide into a more stable hydrated oxide.

The film thickness of the anodic oxide film is preferably from 0.3 μm to 15 μm. When the thickness of the anodic oxide film is within the above range, a barrier property against injection tends to be exerted and an increase in the residual potential due to the repeated use tends to be prevented.

The conductive substrate may be subjected to a treatment with an acidic aqueous solution or a boehmite treatment.

The treatment with an acidic treatment solution is carried out as follows. First, an acidic treatment solution including phosphoric acid, chromic acid, and hydrofluoric acid is prepared. The mixing ratio of phosphoric acid, chromic acid, and hydrofluoric acid in the acidic treatment solution is, for example, a ratio such that from 10% by weight to 11% by weight of phosphoric acid, from 3% by weight to 5% by weight of chromic acid, and from 0.5% by weight to 2% by weight of hydrofluoric acid. The concentration of the total acid components is preferably in the range of 13.5% by weight to 18% by weight. The treatment temperature is, for example, preferably from 42° C. to 48° C. The film thickness of the film is preferably from 0.3 μm to 15 μm.

The boehmite treatment is carried out by immersing the substrate in pure water at a temperature of 90° C. to 100° C. for 5 minutes to 60 minutes, or by bringing it into contact with heated water vapor at a temperature of 90° C. to 120° C. for 5 minutes to 60 minutes. The film thickness of the film is preferably from 0.1 μm to 5 μm. The film may further be subjected to an anodic oxidation treatment using an electrolyte solution which sparingly dissolves the film, such as adipic acid, boric acid, borate, phosphate, phthalate, maleate, benzoate, tartrate, and citrate solutions.

Undercoat Layer

The undercoat layer is, for example, a layer including inorganic particles and a binder resin.

Examples of the inorganic particles include inorganic particles having powder resistance (volume resistivity) of about $10^2$ Ωcm to $10^{11}$ Ωcm.

Among these, as the inorganic particles having the resistance values above, metal oxide particles such as tin oxide particles, titanium oxide particles, zinc oxide particles, and zirconium oxide particles are preferable, and zinc oxide particles are more preferable.

The specific surface area of the inorganic particles as measured by a BET method is, for example, preferably 10 m$^2$/g or more.

The volume average particle diameter of the inorganic particles is, for example, preferably from 50 nm to 2000 nm (preferably from 60 nm to 1000 nm).

The content of the inorganic particles is, for example, preferably from 10% by weight to 80% by weight, and more preferably from 40% by weight to 80% by weight, based on the binder resin.

The inorganic particles may be the ones which have been subjected to a surface treatment. The inorganic particles which have been subjected to different surface treatments or have different particle diameters may be used in combination of two or more kinds.

Examples of the surface treatment agent include a silane coupling agent, a titanate coupling agent, an aluminum coupling agent, and a surfactant. Particularly, the silane coupling agent is preferable, and a silane coupling agent having an amino group is more preferable.

Examples of the silane coupling agent having an amino group include 3-aminopropyltriethoxysilane, N-2-(aminoethyl)-3-aminopropyltrimethoxysilane, N-2-(aminoethyl)-3-aminopropylmethyldimethoxysilane, and N,N-bis(2-hydroxyethyl)-3-aminopropyltriethoxysilane, but are not limited thereto.

These silane coupling agents may be used as a mixture of two or more kinds thereof. For example, a silane coupling agent having an amino group and the other silane coupling agent may be used in combination. Examples of the other silane coupling agent include vinyltrimethoxysilane, 3-methacryloxypropyl-tris(2-methoxyethoxy)silane, 2-(3,4-epoxycyclohexyl)ethyltrimethoxysilane, 3-glycidoxypropyltrimethoxysilane, vinyltriacetoxysilane, 3-mercaptopropyltrimethoxysilane, 3-aminopropyltriethoxysilane, N-2-(aminoethyl)-3-aminopropyltrimethoxysilane, N-2-(aminoethyl)-3-aminopropylmethyldimethoxysilane, N,N-bis(2-hydroxyethyl)-3-aminopropyltriethoxysilane, and 3-chloropropyltrimethoxysilane, but are not limited thereto.

The surface treatment method using a surface treatment agent may be any one of known methods, and may be either a dry method or a wet method.

The amount of the surface treatment agent for treatment is, for example, preferably from 0.5% by weight to 10% by weight, based on the inorganic particles.

Here, inorganic particles and an electron acceptive compound (acceptor compound) are preferably included in the undercoat layer from the viewpoint of superior long-term stability of electrical characteristics and carrier blocking property.

Examples of the electron acceptive compound include electron transport materials such as quinone compounds such as chloranil and bromanil; tetracyanoquinodimethane compounds; fluorenone compounds such as 2,4,7-trinitrofluorenone and 2,4,5,7-tetranitro-9-fluorenone; oxadiazole compounds such as 2-(4-biphenyl)-5-(4-t-butylphenyl)-1,3,4-oxadiazole, 2,5-bis(4-naphthyl)-1,3,4-oxadiazole, and 2,5-bis(4-diethylaminophenyl)-1,3,4-oxadiazole; xanthone compounds; thiophene compounds; and diphenoquinone compounds such as 3,3',5,5'-tetra-t-butyldiphenoquinone.

Particularly, as the electron acceptive compound, compounds having an anthraquinone structure are preferable. As the electron acceptive compounds having an anthraquinone structure, hydroxyanthraquinone compounds, aminoanthraquinone compounds, aminohydroxyanthraquinone compounds, and the like are preferable, and specifically, anthraquinone, alizarin, quinizarin, anthrarufin, purpurin, and the like are preferable.

The electron acceptive compound may be included as dispersed with the inorganic particles in the undercoat layer, or may be included as attached to the surface of the inorganic particles.

Examples of the method of attaching the electron acceptive compound to the surface of the inorganic particles include a dry method and a wet method.

The dry method is a method for attaching an electron acceptive compound to the surface of the inorganic particles, in which the electron acceptive compound is added dropwise to the inorganic particles or sprayed thereto together with dry air or nitrogen gas, either directly or in the form of a solution in which the electron acceptive compound is dissolved in an organic solvent, while the inorganic particles are stirred with a mixer or the like having a high shearing force. The addition or spraying of the electron acceptive compound is preferably carried out at a temperature not higher than the boiling point of the solvent. After the addition or spraying of the electron acceptive compound, the inorganic particles may further be subjected to baking at a temperature of 100° C. or higher. The baking may be carried out at any temperature and time without limitation, by which desired electrophotographic characteristics may be obtained.

The wet method is a method for attaching an electron acceptive compound to the surface of the inorganic particles, in which the inorganic particles are dispersed in a solvent by means of stirring, ultrasonic wave, a sand mill, an attritor, a ball mill, or the like, then the electron acceptive compound is added and the mixture is further stirred or dispersed, and thereafter, the solvent is removed. As a method for removing the solvent, the solvent is removed by filtration or distillation. After removing the solvent, the particles may further be subjected to baking at a temperature of 100° C. or higher. The baking may be carried out at any temperature and time without limitation, in which desired electrophotographic characteristics may be obtained. In the wet method, the moisture contained in the inorganic particles may be removed prior to the addition of an electron acceptive compound, and examples of a method for removing the moisture include a method for removing the moisture by stirring and heating the inorganic particles in a solvent or by azeotropic removal with the solvent.

Furthermore, the attachment of the electron acceptive compound may be carried out before or after the inorganic particles are subjected to a surface treatment using a surface treatment agent, and the attachment of the electron acceptive compound may be carried out at the same time with the surface treatment using a surface treatment agent.

The content of the electron acceptive compound is, for example, preferably from 0.01% by weight to 20% by weight, and more preferably from 0.01% by weight to 10% by weight, based on the inorganic particles.

Examples of the binder resin used in the undercoat layer include known materials, such as well-known polymeric compounds such as acetal resins (for example, polyvinylbutyral), polyvinyl alcohol resins, polyvinyl acetal resins, casein resins, polyamide resins, cellulose resins, gelatins, polyurethane resins, polyester resins, unsaturated polyether resins, methacrylic resins, acrylic resins, polyvinyl chloride resins, polyvinyl acetate resins, vinyl chloride-vinyl acetate-maleic anhydride resins, silicone resins, silicone-alkyd resins, urea resins, phenol resins, phenol-formaldehyde resins, melamine resins, urethane resins, alkyd resins, and epoxy resins; zirconium chelate compounds; titanium chelate compounds; aluminum chelate compounds; titaniumalkoxide compounds; organic titanium compounds; and silane coupling agents.

Other examples of the binder resin used in the undercoat layer include charge transport resins having charge transport groups, and conductive resins (for example, polyaniline).

Among these, as the binder resin used in the undercoat layer, a resin which is insoluble in a coating solvent of an upper layer is suitable, and particularly, thermosetting resins such as urea resins, phenol resins, phenol-formaldehyde resins, melamine resins, urethane resins, unsaturated polyester resins, alkyd resins, and epoxy resins; and resins obtained by a reaction of a curing agent and at least one kind of resin selected from the group consisting of polyamide resins, polyester resins, polyether resins, methacrylic resins, acrylic resins, polyvinyl alcohol resins, and polyvinyl acetal resins are suitable.

In the case where these binder resins are used in combination of two or more kinds thereof, the mixing ratio is set as appropriate.

Various additives may be used for the undercoat layer to improve electrical characteristics, environmental stability, or image quality.

Examples of the additives include known materials such as the polycyclic condensed type or azo type of the electron transport pigments, zirconium chelate compounds, titanium chelate compounds, aluminum chelate compounds, titanium alkoxide compounds, organic titanium compounds, and silane coupling agents. A silane coupling agent, which is used for surface treatment of inorganic particles as described above, may also be added to the undercoat layer as an additive.

Examples of the silane coupling agent as an additive include vinyltrimethoxysilane, 3-methacryloxypropyl-tris(2-methoxyethoxy)silane, 2-(3,4-epoxycyclohexyl)ethyltrimethoxysilane, 3-glycidoxypropyltrimethoxysilane, vinyltriacetoxysilane, 3-mercaptopropyltrimethoxysilane, 3-aminopropyltriethoxysilane, N-2-(aminoethyl)-3-aminopropyltrimethoxysilane, N-2-(aminoethyl)-3-aminopropylmethylmethoxysilane, N,N-bis(2-hydroxyethyl)-3-aminopropyltriethoxysilane, and 3-chloropropyltrimethoxysilane.

Examples of the zirconium chelate compounds include zirconium butoxide, zirconium ethylacetoacetate, zirconium triethanolamine, acetylacetonate zirconium butoxide, ethylacetoacetate zirconium butoxide, zirconium acetate, zirconium oxalate, zirconium lactate, zirconium phosphonate, zirconium octanoate, zirconium naphthenate, zirconium laurate, zirconium stearate, zirconium isostearate, methacrylate zirconium butoxide, stearate zirconium butoxide, and isostearate zirconium butoxide.

Examples of the titanium chelate compounds include tetraisopropyl titanate, tetranormalbutyl titanate, butyl titanate dimer, tetra(2-ethylhexyl) titanate, titanium acetyl acetonate, polytitaniumacetyl acetonate, titanium octylene glycolate, titanium lactate ammonium salt, titanium lactate, titanium lactate ethyl ester, titanium triethanol aminate, and polyhydroxy titanium stearate.

Examples of the aluminum chelate compounds include aluminum isopropylate, monobutoxy aluminum diisopropylate, aluminum butylate, diethylacetoacetate aluminum diisopropylate, and aluminum tris(ethylacetoacetate).

These additives may be used alone, or as a mixture or a polycondensate of plural compounds.

The Vickers hardness of the undercoat layer is preferably 35 or more.

The surface roughness (ten point height of irregularities) of the undercoat layer is adjusted in the range of from $(1/4)n\lambda$ to $(1/2)\lambda$, in which X represents the wavelength of the laser for exposure and n represents a refractive index of the upper layer, in order to prevent a moire image.

Resin particles and the like may be added in the undercoat layer in order to adjust the surface roughness. Examples of the resin particles include silicone resin particles and crosslinked polymethyl methacrylate resin particles. In addition, the surface of the undercoat layer may be polished in order to adjust the surface roughness. Examples of the polishing method include buffing grinding, a sandblasting treatment, wet honing, and a grinding treatment.

The formation of the undercoat layer is not particularly limited, and well-known forming methods are used. However, the formation of the undercoat layer is carried out by, for example, forming a coating film by a coating liquid for forming an undercoat layer, which is obtained by adding the components above to a solvent, and drying the coating film, followed by heating, as desired.

Examples of the solvent for forming the coating liquid for forming an undercoat layer include known organic solvents, such as alcohol solvents, aromatic hydrocarbon solvents, hydrocarbon halide solvents, ketone solvents, ketone alcohol solvents, ether solvents, and ester solvents.

Specific examples of these solvents include ordinary organic solvents such as methanol, ethanol, n-propanol, isopropanol, n-butanol, benzyl alcohol, methyl cellosolve, ethyl cellosolve, acetone, methyl ethyl ketone, cyclohexanone, methyl acetate, ethyl acetate, n-butyl acetate, dioxane, tetrahydrofuran, methylene chloride, chloroform, chlorobenzene, and toluene.

Examples of a method for dispersing inorganic particles in preparing the coating liquid for forming an undercoat layer include known methods such as methods using a roll mill, a ball mill, a vibration ball mill, an attritor, a sand mill, a colloid mill, a paint shaker, and the like.

Examples of a method for coating the coating liquid for forming an undercoat layer onto a conductive substrate include ordinary methods such as a blade coating method, a wire bar coating method, a spray coating method, a dip coating method, a bead coating method, an air knife coating method, and a curtain coating method.

The film thickness of the undercoat layer is set to a range of, for example, preferably 15 µm or more, and more preferably from 20 µm to 50 µm.

Intermediate Layer

Although not shown in the figures, an intermediate layer may be provided between the undercoat layer and the photosensitive layer.

The intermediate layer is, for example, a layer including a resin. Examples of the resin used in the intermediate layer include polymeric compounds such as acetal resins (for example, polyvinylbutyral), polyvinyl alcohol resins, polyvinyl acetal resins, casein resins, polyamide resins, cellulose resins, gelatins, polyurethane resins, polyester resins, methacrylic resins, acrylic resins, polyvinyl chloride resins, polyvinyl acetate resins, vinyl chloride-vinyl acetate-maleic anhydride resins, silicone resins, silicone-alkyd resins, phenol-formaldehyde resins, and melamine resins.

The intermediate layer may be a layer including an organic metal compound. Examples of the organic metal compound used in the intermediate layer include organic metal compounds containing a metal atom such as zirconium, titanium, aluminum, manganese, and silicon.

These compounds used in the intermediate layer may be used alone or as a mixture or a polycondensate of plural compounds.

Among these, the intermediate layer is preferably a layer including an organometallic compound containing a zirconium atom or a silicon atom.

The formation of the intermediate layer is not particularly limited, and well-known forming methods are used. However, the formation of the intermediate layer is carried out, for example, by forming a coating film by a coating liquid for forming an intermediate layer, which is obtained by adding the components above to a solvent, and drying the coating film, followed by heating, as desired.

As a coating method for forming an intermediate layer, ordinary methods such as a dip coating method, an extrusion coating method, a wire bar coating method, a spray coating method, a blade coating method, a knife coating method, and a curtain coating method are used.

The film thickness of the intermediate layer is set to, for example, preferably a range of 0.1 μm to 3 μm. Further, the intermediate layer may be used as an undercoat layer.

Single Layer Type Photosensitive Layer

The single layer type photosensitive layer may include a binder resin, a charge generating material, a hole transport material, and an electron transport material, and other additives, as desired.

Binder Resin

The binder resin is not particularly limited, but examples thereof include polycarbonate resins, polyester resins, polyarylate resins, methacrylic resins, acrylic resins, polyvinyl chloride resins, polyvinylidene chloride resins, polystyrene resins, polyvinyl acetate resins, styrene-butadiene copolymers, vinylidene chloride-acrylonitrile copolymers, vinyl chloride-vinyl acetate copolymers, vinyl chloride-vinyl acetate-maleic anhydride copolymers, silicone resins, silicone-alkyd resins, phenol-formaldehyde resins, styrene-alkyd resins, poly-N-vinyl carbazole, and polysilane. These binder resins may be used alone or as a mixture of two or more kinds thereof.

Among these binder resins, from the viewpoint of prevention of segregation of electron transport materials, particularly, polycarbonate resins and polyarylate resins are preferable.

Further, from the viewpoint of film-forming property of a photosensitive layer, as the binder resin, for example, polycarbonate resins having a viscosity average molecular weight of 30000 to 80000 and polyarylate resins having a viscosity average molecular weight of 30000 to 80000 are preferable.

Further, the viscosity average molecular weight is measured as follows. Specifically, 1 g of a resin is dissolved in 100 cm³ of methylene chloride, and the specific viscosity ηsp is measured under the measurement condition of 25° C. using an Ubbellohde's viscometer. Further, an intrinsic viscosity (η) (cm³/g) is determined from a relationship equation of ηsp/c=(η)+0.45(η)²c (in which c is a concentration (g/cm³)). Further, a viscosity average molecular weight My is determined from an equation given by H. Schnell, (η)=1.23×10⁻⁴ Mv0.83. As such, for measurement of the viscosity average molecular weight, for example, a one-point measurement method is used.

The content of the binder resin based on the total solid content of the photosensitive layer is, for example, from 35% by weight to 60% by weight, and preferably from 40% by weight to 55% by weight.

Charge Generating Material

Examples of the charge generating material include azo pigments such as bisazo and trisazo pigments; condensed aromatic pigments such as dibromoanthanthrone pigments; perylene pigments; pyrrolopyrrole pigments; phthalocyanine pigments; zinc oxides; and trigonal selenium.

Among these, in order to correspond to laser exposure in the near-infrared region, it is preferable to use metal phthalocyanine pigments or metal-free phthalocyanine pigments as the charge generating material, and specifically, hydroxygallium phthalocyanine disclosed in JP-A-5-263007, JP-A-5-279591, and the like; chlorogallium phthalocyanine disclosed in JP-A-5-98181 and the like; dichlorotin phthalocyanine disclosed in JP-A-5-140472, JP-A-5-140473, and the like; and titanyl phthalocyanine disclosed in JP-A-4-189873 and the like are more preferable.

On the other hand, in order to correspond to laser exposure in the near-ultraviolet region, as the charge generating material, condensed aromatic pigments such as dibromoanthanthrone; thioindigo pigments; porphyrazine compounds; zinc oxides; trigonal selenium; bisazo pigments disclosed in JP-A-2004-78147 and JP-A-2005-181992; and the like are preferable.

That is, as the charge generating material, an inorganic pigment is preferable to correspond to a case where a light source having an exposure wavelength of from 380 nm to 500 nm is used, and, a metal phthalocyanine pigment or a metal-free phthalocyanine pigment is preferable to correspond to a case where a light source having an exposure wavelength of from 700 nm to 800 nm is used.

In the exemplary embodiment, as the charge generating material, at least one selected from a hydroxygallium phthalocyanine pigment and a chlorogallium phthalocyanine pigment is preferably used.

As the charge generating material, these pigments may be used alone or in combination thereto, as desired. Further, as the charge generating material, a hydroxygallium phthalocyanine pigment is preferable from the viewpoints of a high sensitivity of a photoreceptor and prevention of dot defects of an image.

The hydroxygallium phthalocyanine pigment is not particularly limited, but a V-type hydroxygallium phthalocyanine pigment is preferable.

Particularly, as the hydroxygallium phthalocyanine pigment, for example, a hydroxygallium phthalocyanine pigment having a maximum peak wavelength in the range of from 810 nm to 839 nm in a spectral absorption spectrum in a wavelength region of from 600 nm to 900 nm is preferable from the viewpoint that it imparts more excellent dispersibility. When the hydroxygallium phthalocyanine pigment is used as a material for an electrophotographic photoreceptor, excellent dispersibility, sufficient sensitivity, chargeability, and characteristics of dark attenuation are easily obtained.

Further, the hydroxygallium phthalocyanine pigment having a maximum peak wavelength in the range from 810 nm to 839 nm preferably has an average particle diameter in a specific range and a BET specific surface area in a specific range. On the other hand, the average particle diameter is preferably 0.20 μm or less, and more preferably from 0.01 μm to 0.15 μm. On the other hand, the BET specific surface area is preferably 45 m²/g or more, more preferably 50 m²/g or more, and particularly preferably from 55 m²/g to 120 m²/g. An average particle diameter is a volume average particle diameter (d50 average particle diameter) and a value measured by a laser diffraction scattering particle size distribution analyzer LA-700 (manufactured by Horiba Ltd.). Further, the BET specific surface area is a value measured by a nitrogen substitution method using a BET specific surface area analyzer (FLOWSORB 112300, manufactured by Shimadzu Corporation).

Here, in the case where the average particle diameter is more than 0.20 μm or the specific surface area value is less than 45 m²/g, the pigment particles are coarsened or aggregates of pigment particles are formed. Further, the characteristics such as dispersibility, sensitivity, chargeability, and dark attenuation characteristics tend to be deteriorated to result in image defect in some cases.

A maximum particle diameter (a maximum value of a primary particle diameter) of the hydroxygallium phthalocyanine pigment is preferably 1.2 μm or less, more preferably 1.0 μm or less, and still more preferably 0.3 μm or less. When the maximum particle diameter exceeds the above range, black spots tend to be formed.

From the viewpoint of preventing the density unevenness caused by exposing a photoreceptor to a fluorescent lamp or the like from occurring, the hydroxygallium phthalocyanine pigment preferably has an average particle diameter of 0.2 μm or less, the maximum particle diameter of 1.2 μm or less and the specific surface area of 45 m²/g or more.

The hydroxygallium phthalocyanine pigment is preferably a V type one which has diffraction peaks at at least 7.3°, 16.0°, 24.9°, and 28.0° by a Bragg angle (2θ±0.2°) in an X-ray diffraction spectrum obtained using CuKα characteristic X-ray.

On the other hand, the chlorogallium phthalocyanine pigment is not particularly limited, but preferably has diffraction peaks at 7.4°, 16.6°, 25.5°, and 28.3° by a Bragg angle (2θ±0.20) in an X-ray diffraction spectrum obtained using CuKα characteristic X-ray, whereby excellent sensitivity for an electrophotographic photoreceptor material is obtained.

Suitable maximum peak wavelength of the spectral absorption spectrum, the average particle diameter, the maximum particle diameter, and the specific surface area value of the chlorogallium phthalocyanine pigment are the same as those of the hydroxygallium phthalocyanine pigment.

The content of the charge generating material based on the total solid content of the photosensitive layer is preferably from 1% by weight to 5% by weight, and more preferably from 1.2% by weight to 4.5% by weight.

Hole Transport Material

Examples of the hole transport material include triarylamine compounds, benzidine compounds, arylalkane compounds, aryl-substituted ethylene compounds, stilbene compounds, anthracene compounds, and hydrazone compounds. These charge transport materials may be used alone or in combination of two or more kinds thereof, but are not limited thereto.

The hole transport material is preferably a compound represented by the following formula (B-1), a compound represented by the following formula (B-2), and a compound represented by the following formula (B-3) from the viewpoint of charge mobility.

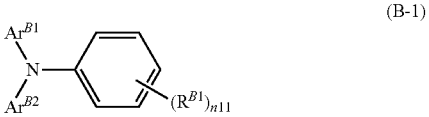

In the formula (B-1), $R^{B1}$ represents a hydrogen atom or a methyl group. n11 represents 1 or 2. $Ar^{B1}$ and $Ar^{B2}$ each independently represent a substituted or unsubstituted aryl group, $-C_6H_4-C(R^{B3})=C(R^{B4})(R^{B5})$, or $-C_6H_4-CH=CH-CH=C(R^{B6})(R^{B7})$, and $R^{B3}$ to $R^{B7}$ each independently represent a hydrogen atom, a substituted or unsubstituted alkyl group, or a substituted or unsubstituted aryl group. The substituent represents a halogen atom, an alkyl group having 1 to 5 carbon atoms, an alkoxy group having 1 to 5 carbon atoms, or a substituted amino group substituted with an alkyl group having 1 to 3 carbon atoms.

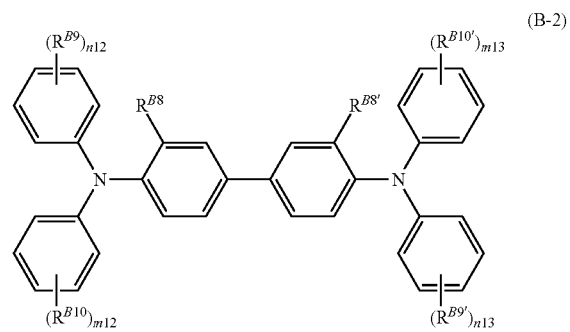

In the formula (B-2), $R^{B8}$ and $R^{B8'}$ may be the same as or different from each other and each independently represent a hydrogen atom, a halogen atom, an alkyl group having 1 to 5 carbon atoms, or an alkoxy group having 1 to 5 carbon atoms. $R^{B9}$, $R^{B9'}$, $R^{B10'}$, and $R^{B10'}$ may be the same as or different from each other and each independently represent a halogen atom, an alkyl group having 1 to 5 carbon atoms, an alkoxy group having 1 to 5 carbon atoms, a substituted amino group substituted with an alkyl group having 1 or 2 carbon atoms, a substituted or unsubstituted aryl group, $-C(R^{B11})=C(R^{B12})(R^{B13})$, or $-CH=CH-CH=C(R^{B14})(R^{B15})$, and $R^{B1}$ to $R^{B15}$ each independently represent a hydrogen atom, a substituted or unsubstituted alkyl group, or a substituted or unsubstituted aryl group. m12, m13, n12, and n13 each independently represent an integer of 0 to 2.

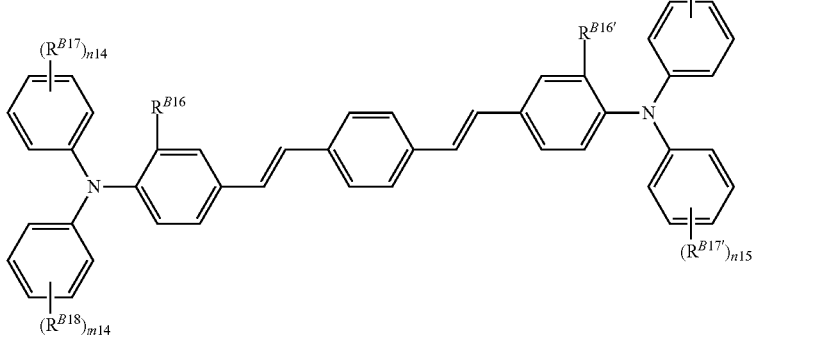

In the formula (B-3), $R^{B16}$ and $R^{B16'}$ may be the same as or different from each other and each independently represent a hydrogen atom, a halogen atom, an alkyl group having 1 to 5 carbon atoms, or an alkoxy group having 1 to 5 carbon atoms. $R^{B17}$, $R^{B17'}$, $R^{B18}$, and $R^{B18'}$ may be the same as or different from each other and each independently represent a halogen atom, an alkyl group having 1 to 5 carbon atoms, an alkoxy group having 1 to 5 carbon atoms, a substituted amino group substituted with an alkyl group having 1 or 2 carbon atoms, a substituted or unsubstituted aryl group, —C($R^{B19}$)=C($R^{B20}$) ($R^{B21}$), or —CH=CH—CH=C($R^{B22}$) ($R^{B23}$), and $R^{B19}$ to $R^{B23}$ each independently represent a hydrogen atom, a substituted or unsubstituted alkyl group, or a substituted or unsubstituted aryl group. m14, m15, n14, and n15 each independently represent an integer of 0 to 2.

Here, among the compound represented by the formula (B-1), the compound represented by the formula (B-2), and the compound represented by the formula (B-3), the compound represented by the formula (B-1) having "—$C_6H_4$—CH=CH—CH=C($R^{B6}$) ($R^{B7}$)" and the compound represented by the formula (B-2) having "—CH=CH—CH=C($R^{B14}$) ($R^{B15}$)" are preferable.

Specific examples of the compound represented by the formula (B-1), the compound represented by the formula (B-2), and the compound represented by the formula (B-3) include the following compounds.

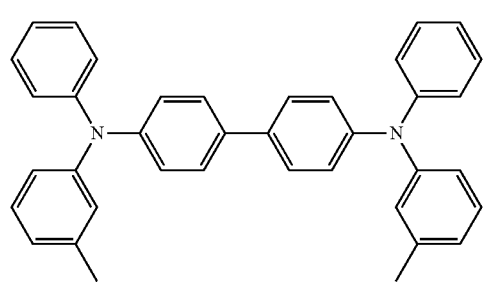

HT-1

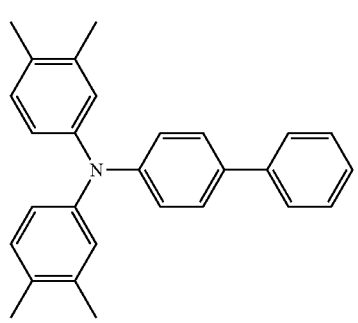

HT-2

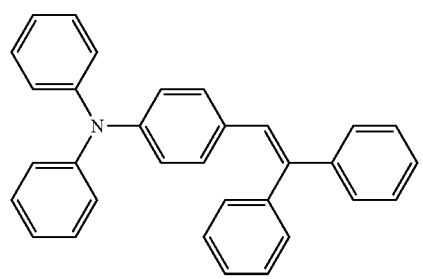

HT-3

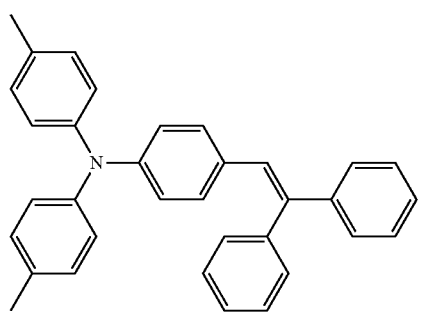

HT-4

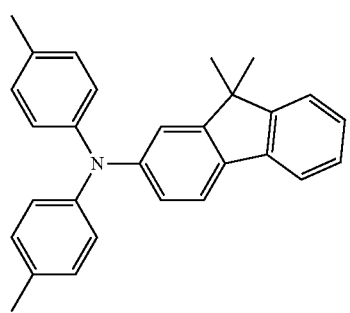

HT-5

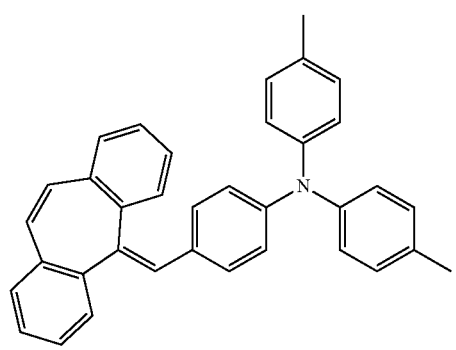

HT-6

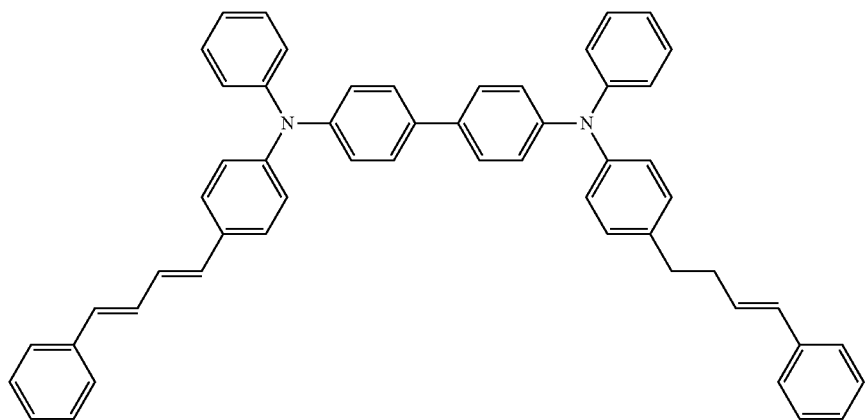
HT-7
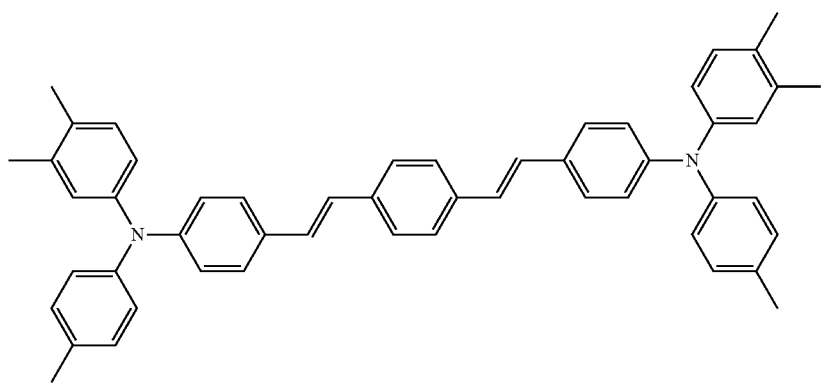
HT-8
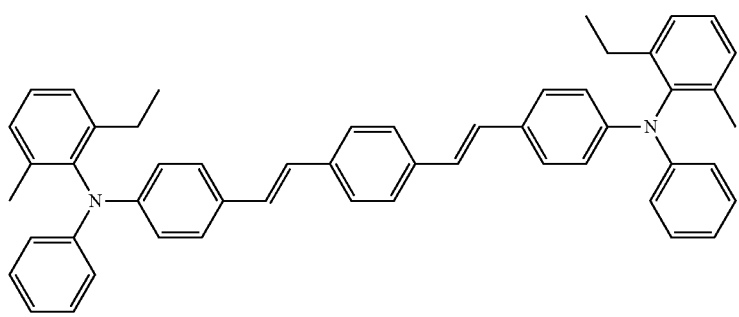
HT-9

-continued

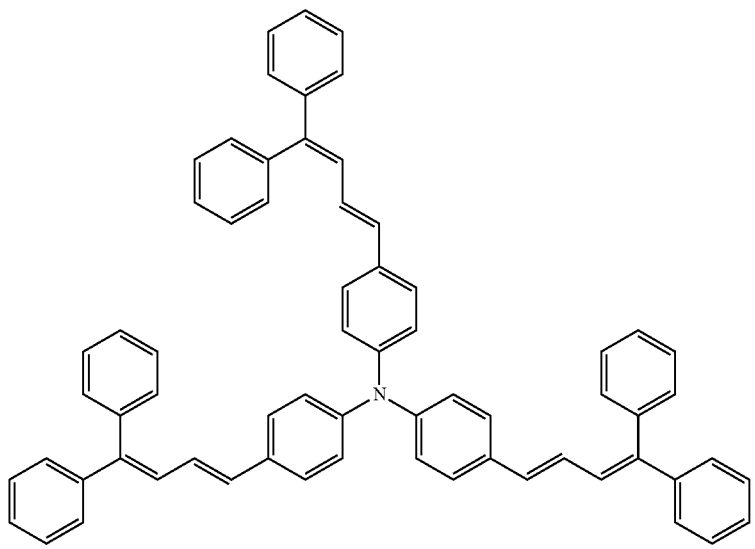

HT-10

The content of the hole transport material based on the total solid content of the photosensitive layer is preferably from 10% by weight to 40% by weight, and more preferably from 20% by weight to 35% by weight. Further, the content of the hole transport material is the content of the entire hole transport materials in the case of using a combination of plural kinds of hole transport materials.

Electron Transport Material

As the electron transport material, at least an electron transport material represented by the formula (1) is used, but may be used alone, or may be used in combination of other electron transport materials, as desired, within a range not adversely affecting the invention.

The content of the electron transport material represented by the formula (1) based on the total solid content of the photosensitive layer is preferably from 1% by weight to 30% by weight, and more preferably from 5% by weight to 20% by weight. By setting the content of the electron transport material represented by the formula (1) based on the total solid content of the photoreceptor to the above range, as compared with a case where the content of the electron transport material represented by the formula (1) is less, the electrical characteristics of the photoreceptor becomes better, whereas as compared with a case where the content of the electron transport material represented by the formula (1) is more than the range, fog or color dots are hardly formed on an image thus formed.

Further, in the case where other electron transport materials are used as the electron transport material, it is preferable to use other electron transport materials in the amount of 50% by weight or less based on the total amount of the electron transport material.

Examples of the other electron transport materials include electron transport compounds, such as fluorenone derivatives other than the electron transport material represented by the formula (1); quinone compounds such as p-benzoquinone, chloranil, bromanil, and anthraquinone; tetracyanoquinodimethane compounds; fluorenone compounds such as 2,4,7-trinitrofluorenone; xanthone compounds; benzophenone compounds; cyanovinyl compounds; and ethylene compounds. These other charge transport materials may be used alone or in combination of two or more kinds thereof, but are not limited thereto.

Specific examples of the other electron transport material include the following compounds.

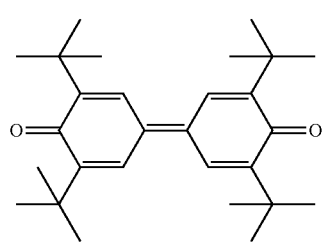

ET-A

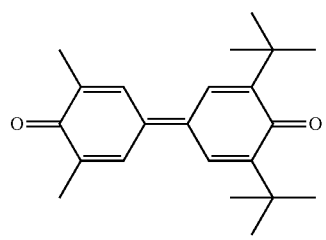

ET-B

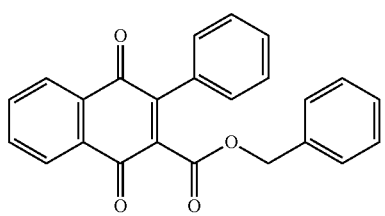

ET-C

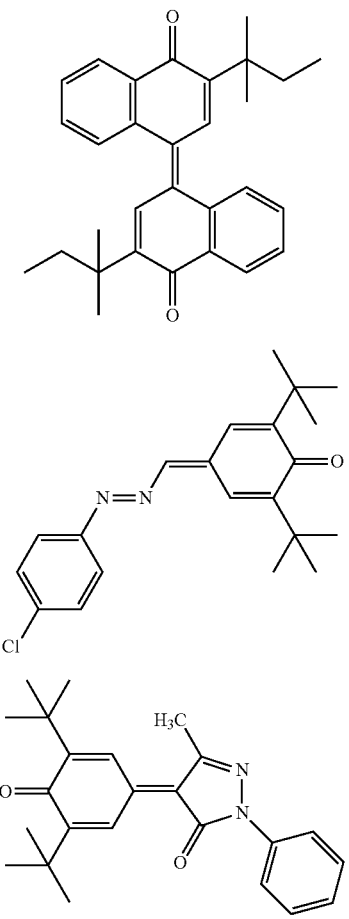

ET-E

ET-F

ET-G

The ratio of the hole transport material to the electron transport material is preferably from 50/50 to 90/10, and more preferably from 60/40 to 80/20, in terms of a weight ratio (hole transport material/electron transport material).

In addition, in the case of using other electron transport materials in combination, the "electron transport materials" in this ratio is a sum of the combination of the materials.

Other Additives

The single layer type photosensitive layer may include other known additives such as a surfactant, an antioxidant, a light stabilizer, and a heat stabilizer. Further, in the case where the single layer type photosensitive layer is a surface layer, it may include fluorine resin particles, silicone oils, or the like.

Formation of Single Layer Type Photosensitive layer

The single layer type photosensitive layer is formed by using a coating liquid for forming a photosensitive layer, which is prepared by adding the above components in a solvent.

Examples of the solvent include ordinary organic solvents, such as aromatic hydrocarbons such as benzene, toluene, xylene, and chlorobenzene; ketones such as acetone and 2-butanone; aliphatic hydrocarbon halides such as methylene chloride, chloroform, and ethylene chloride; and cyclic or linear ethers such as tetrahydrofuran and ethyl ether. These solvents may be used alone or in combination of two or more kinds thereof.

For a method for dispersing particles (for example, charge generating materials) in the coating liquid for forming a photosensitive layer, for example, a media dispersing machine such as a ball mill, a vibrating ball mill, an attritor, a sand mill, and a horizontal sand mill, or a medialess dispersing machine such as a stirrer, an ultrasonic dispersing machine, a roll mill, and a high-pressure homogenizer is used. Examples of the high-pressure homogenizer include a collision system in which the particles are dispersed by causing the dispersion to collide against liquid or against walls under a high pressure, and a penetration system in which the particles are dispersed by causing the dispersion to penetrate through a fine flow path under a high pressure.

Examples of a method for coating the coating liquid for forming a photosensitive layer onto the undercoat layer include a dip coating method, an extrusion coating method, a wire bar coating method, a spray coating method, a blade coating method, a knife coating method, and a curtain coating method.

The film thickness of the single layer type photosensitive layer is set to a range of preferably from 5 μm to 60 m, more preferably from 5 μm to 50 μm, and still more preferably from 10 μm to 40 μm.

Image Forming Apparatus (and Process Cartridge)

The image forming apparatus according to the present exemplary embodiment is provided with an electrophotographic photoreceptor, a charging unit that charges the surface of the electrophotographic photoreceptor, an electrostatic latent image forming unit that forms an electrostatic latent image on the surface of a charged electrophotographic photoreceptor, a developing unit that develops the electrostatic latent image formed on the surface of the electrophotographic photoreceptor by a developer including a toner to form a toner image, and a transfer unit that transfers the toner image onto a surface of a recording medium. Further, the electrophotographic photoreceptor according to the present exemplary embodiment is applied as the electrophotographic photoreceptor.

As the image forming apparatus according to the present exemplary embodiment, known image forming apparatuses provided with a device including a fixing unit that fixes a toner image transferred to the surface of a recording medium; a direct transfer type device that directly transfers the toner image formed on the surface of the electrophotographic photoreceptor to a recording medium; an intermediate transfer type device that primarily transfers the toner image formed on the surface of the electrophotographic photoreceptor on the surface of the intermediate transfer member, and secondarily transfers the toner image transferred to the surface of an intermediate transfer member to the surface of the recording medium; a device provided with a cleaning unit that cleans the surface of the electrophotographic photoreceptor before charging, after the transfer of the toner image; a device provided with a charge erasing unit that erases charges by irradiating erasing light onto the surface of an image holing member before charging, after the transfer of the toner image; a device provided with an electrophotographic photoreceptor heating unit that increases the temperature of the electrophotographic photoreceptor to reduce the relative temperature; and the like are applied.

In the case of the intermediate transfer type device case, for the transfer unit, for example, a configuration in which an intermediate transfer member to the surface of which the toner image is transferred, a primary transfer unit that primarily transfers a toner image formed on the surface of an image holding member to the surface of the intermediate transfer member, and a secondary transfer unit that secondarily transfers the toner image transferred to the surface of the intermediate transfer member on the surface of the recording medium is applied.

The image forming apparatus according to the present exemplary embodiment is any one of a dry development type image forming apparatus and a wet development type (development type using a liquid developer) image forming apparatus.

Furthermore, in the image forming apparatus according to the present exemplary embodiment, for example, a part provided with the electrophotographic photoreceptor may be a cartridge structure (process cartridge) that is detachable from an image forming apparatus. As the process cartridge, for example, a process cartridge including the electrophotographic photoreceptor according to the present exemplary embodiment is suitably used. Further, the process cartridge may include, in addition to the electrophotographic photoreceptor, for example, at least one selected from the group consisting of a charging means, an electrostatic latent image forming unit, a developing unit, and a transfer unit.

Hereinafter, one example of the image forming apparatuses according to the present exemplary embodiment is shown, but the present invention is not limited thereto. Further, the main parts shown in the figures are described, and explanation of the others will be omitted.

Figure 2:
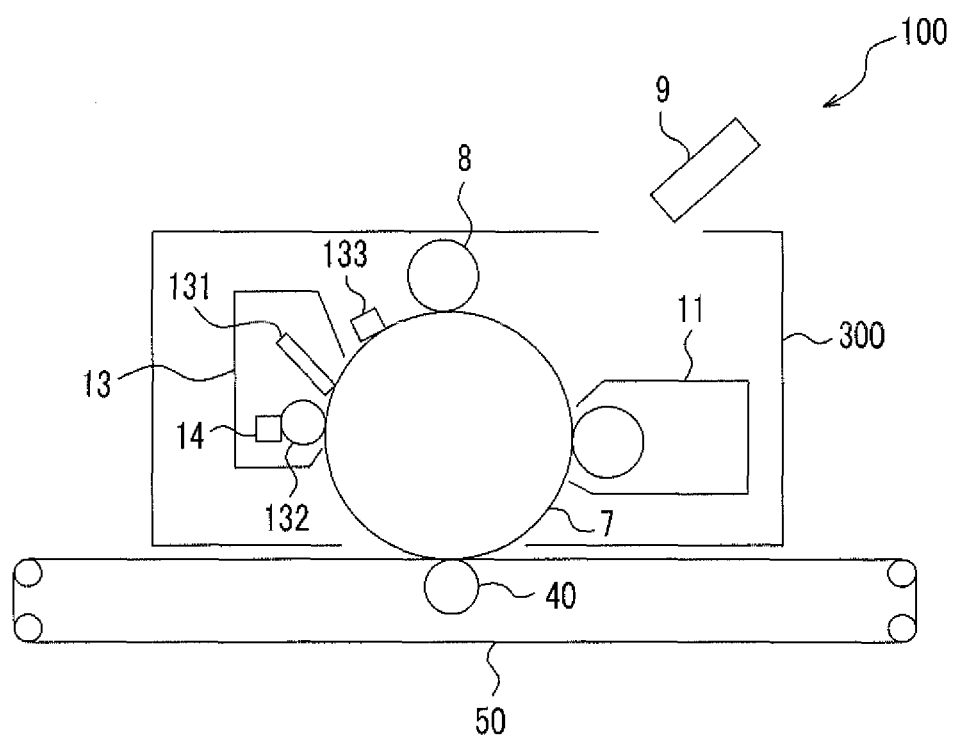
FIG. 2 is a schematic structural view showing an image forming apparatus according to the present exemplary embodiment.

FIG. 2 is a schematic structural view showing an example of the image forming apparatus according to the present exemplary embodiment.

The image forming apparatus 100 according to the present exemplary embodiment is provided with a process cartridge 300 provided with an electrophotographic photoreceptor 7 as shown in FIG. 2, an exposure device 9 (one example of the electrostatic latent image forming unit), a transfer device 40 (primary transfer device), and an intermediate transfer member 50. Further, in the image forming apparatus 100, the exposure device 9 is arranged at a position where the exposure device 9 may radiate light onto the electrophotographic photoreceptor 7 through an opening in the process cartridge 300, and the transfer device 40 is arranged at a position opposite to the electrophotographic photoreceptor 7 by the intermediary of the intermediate transfer member 50. The intermediate transfer member 50 is arranged to contact partially the electrophotographic photoreceptor 7. Further, although not shown in the figure, the apparatus also includes a secondary transfer device that transfers a toner image transferred onto the intermediate transfer member 50 to a recording medium (for example, paper). Further, the intermediate transfer member 50, the transfer device 40 (primary transfer device), and the secondary transfer device (not shown) correspond to an example of the transfer unit.

The process cartridge 300 in FIG. 2 supports, in a housing, the electrophotographic photoreceptor 7, a charging device 8 (one example of the charging unit), a developing device 11 (one example of the developing unit), and a cleaning device 13 (one example of the cleaning unit) integrally. The cleaning device 13 has a cleaning blade (one example of the cleaning member) 131, and the cleaning blade 131 is arranged so as to be in contact with the surface of the electrophotographic photoreceptor 7. Further, the cleaning member is not an embodiment of the cleaning blade 131, may be a conductive or insulating fibrous member, and may be used alone or in combination with the cleaning blade 131.

Furthermore, FIG. 2 shows an example that includes fibrous member 132 (roll shape) that supplies a lubricant 14 to the surface of the electrophotographic photoreceptor 7 as the image forming apparatus, and a fibrous member 133 (flat brush shape) that assists in cleaning, but these members are disposed, as desired.

Hereinafter, the respective configurations of the image forming apparatus according to the present exemplary embodiment will be described.

Charging Device

As the charging device 8, for example, a contact type charging device using a conductive or semiconductive charging roll, a charging brush, a charging film, a charging rubber blade, a charging tube, or the like is used. Further, per se known charging devices, such as a non-contact type roller charging device, and a scorotron charging device and a corotron charging device, each using corona discharge, and the like are also used.

Exposure Device

The exposure device 9 may be an optical instrument for exposure of the surface of the electrophotographic photoreceptor 7, to rays such as a semiconductor laser ray, an LED ray, and a liquid crystal shutter ray according to an image data. The wavelength of the light source may be a wavelength in the range from the spectral sensitivity wavelengths of the electrophotographic photoreceptor. As the wavelengths of semiconductor lasers, near infrared wavelengths that are oscillation wavelengths near 780 nm are predominant. However, the wavelength of the laser ray to be used is not limited to such a wavelength, and a laser having an oscillation wavelength of 600 nm range, or a laser having any oscillation wavelength in the range from 400 nm to 450 nm as a blue laser may be used. In order to form a color image, it is also effective to use a planar light emission type laser light source capable of attaining a multi-beam output.

Developing Device

As the developing device 11, for example, a common developing device, in which a developer is contacted or not contacted for forming an image, may be used. Such a developing device 11 is not particularly limited as long as it has the above-described functions, and may be appropriately selected according to the intended use. Examples thereof include a known developing device in which the single-component or two-component developer is adhered to the electrophotographic photoreceptor 7 using a brush or a roller. Among these, the developing device using developing roller retaining developer on the surface thereof is preferable.

The developer used in the developing device 11 may be a single-component developer formed of a toner alone or a two-component developer formed of a toner and a carrier. Further, the developer may be magnetic or non-magnetic. As the developer, known ones may be applied.

Cleaning Device

As the cleaning device 13, a cleaning blade type device provided with the cleaning blade 131 is used.

Further, in addition to the cleaning blade type, a fur brush cleaning type and a type of performing developing and cleaning at once may also be employed.

Transfer Device

Examples of the transfer device 40 include per se known transfer charging devices, such as a contact type transfer charging device using a belt, a roller, a film, a rubber blade, or the like, a scorotron transfer charging device utilizing corona discharge, and a corotron transfer charging device utilizing corona discharge.

Intermediate Transfer Member

As the intermediate transfer member 50, a form of a belt (intermediate transfer belt) composed of polyimide, polyamideimide, polycarbonate, polyarylate, polyester, rubber, or the like, which is imparted with the semiconductivity, is used. In addition, the intermediate transfer member may also take the form of a drum, in addition to the form of a belt.

Figure 3:
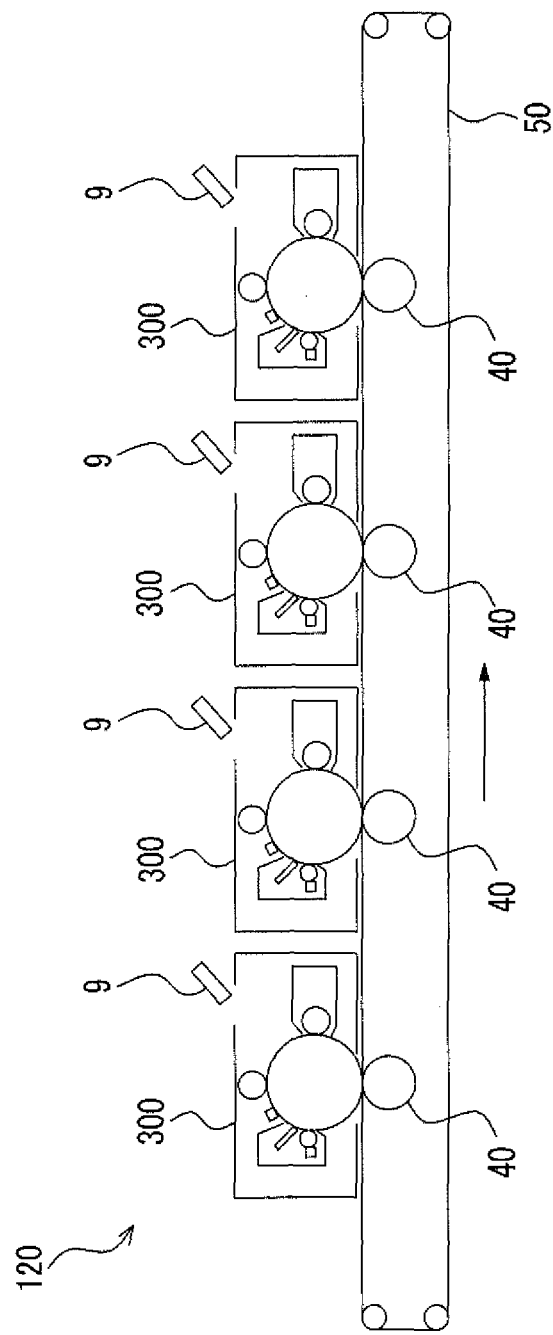
FIG. 3 is another schematic structural view showing an image forming apparatus according to the present exemplary embodiment.

FIG. 3 is a schematic structural view showing another example of the image forming apparatus according to the present exemplary embodiment.

The image forming apparatus 120 shown in FIG. 3 is a tandem type full color image forming apparatus equipped with four process cartridges 300. In the image forming apparatus 120, four process cartridges 300 are disposed parallel with each other on the intermediate transfer member 50, and one electrophotographic photoreceptor may be used for one color.

Further, the image forming apparatus 120 has the same configuration as the image forming apparatus 100, except that it is a tandem type.

Further, the image forming apparatus 100 according to the present exemplary embodiment is not limited to the configuration, and for example, it is in the periphery of the electrophotographic photoreceptor 7. Further, it may be configured to provide a first erasing device for making the erasing with a cleaning brush easier by matching the polarity of the residual toner on the downstream side in the rotating direction of the electrophotographic photoreceptor 7 from the transfer device 40 and on the upstream side in the rotating direction of the electrophotographic photoreceptor from the cleaning device 13, or to provide a second erasing device by erasing the charge of the surface of the electrophotographic photoreceptor 7 on the downstream side in the rotating direction of the electrophotographic photoreceptor from the cleaning device 13 and on the upstream side in the rotating direction of the electrophotographic photoreceptor from the charging device 8.

Furthermore, the image forming apparatus 100 according to the present exemplary embodiment is not limited to the configurations above, and for example, an image forming apparatus having a well-known configuration, in a direct transfer mode, in which a toner image formed in an electrophotographic photoreceptor 7 is directly transferred onto a recording medium, may be employed.

EXAMPLES

Hereinafter, the present invention will be described in more detail with reference to Examples and Comparative Examples, but the invention is not limited to Examples below in any way.

Synthesis of Electron Transport Material

Synthesis Example 1

Synthesis of Exemplary Compound (1-36)

Figure 4:
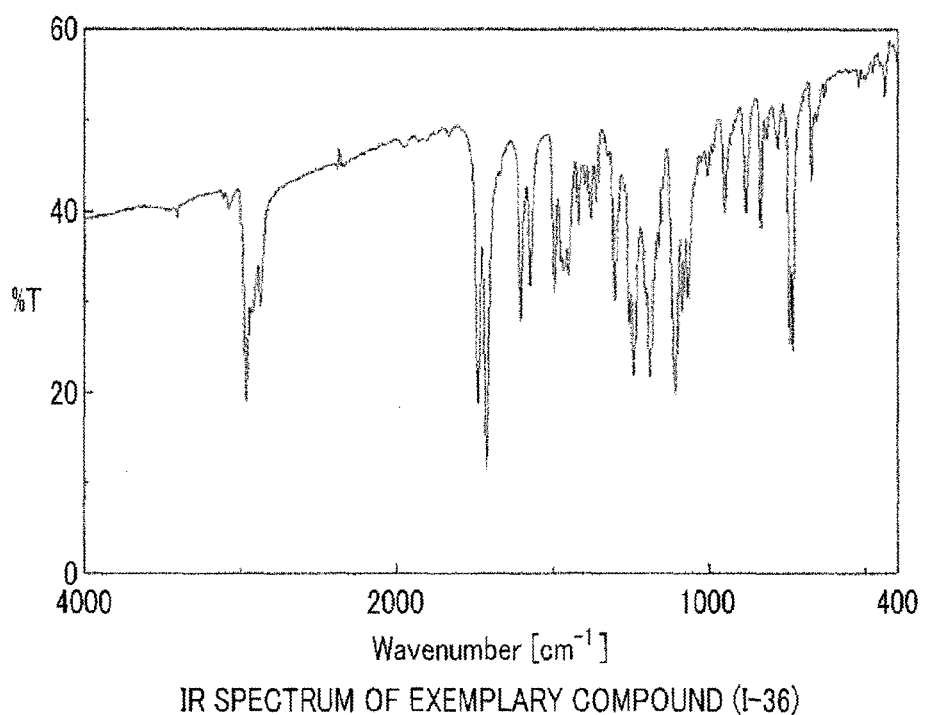
FIG. 4 is a graph showing an infrared absorption spectrum of an exemplary compound (1-36) obtained in Synthesis Example 1.

To 25 g of 9-fluorenone-4-carboxylic acid is added 150 ml of thionyl chloride, followed by heating and stirring at 80° C. for 6 hours. After cooling to room temperature (25° C.), 150 ml of n-hexane is added thereto and the precipitated crystals are filtered to obtain 23 g (yield of 86%) of 9-fluorenone-4-carboxylic acid chloride. Next, to a solution obtained by mixing 15.5 g of 2,4-di-t-pentylphenol, 150 ml of toluene, and 6.7 g of triethylamine is added 14.5 g of 9-fluorenone-4-carboxylic acid chloride obtained above, followed by stirring at room temperature (25° C.) for 48 hours. The reactant is purified by silica gel chromatography to obtain 22 g of an exemplary compound (1-36) which is a desired product. The melting point of the obtained exemplary compound (1-36) is from 164° C. to 167° C. Further, the IR spectrum (infrared absorption spectrum) of the obtained exemplary compound (1-36) is shown in FIG. 4.

Synthesis Example 2

Synthesis of Exemplary Compound (1-37)

Figure 5:
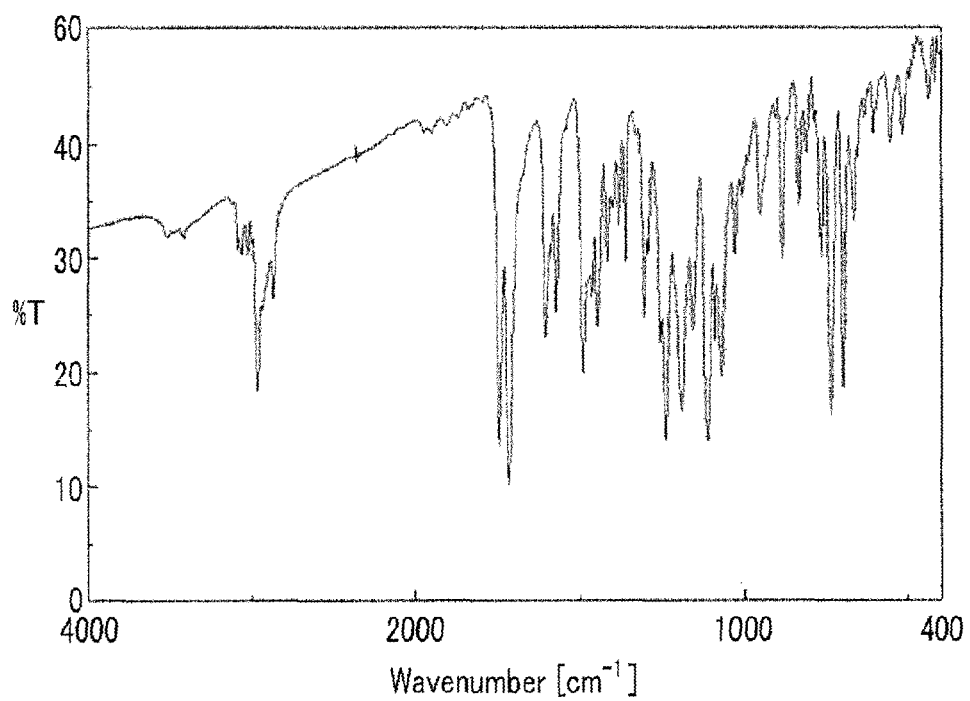
FIG. 5 is a graph showing an infrared absorption spectrum of an exemplary compound (1-37) obtained in Synthesis Example 2.

By performing the synthesis in the same manner as in Synthesis Example 1 except that 15.5 g of 2,4-di-t-pentylphenol of Synthesis Example 1 is changed to 21.8 g of 2,4-bis(α,α-dimethylbenzyl)phenol, 22 g of an exemplary compound (1-37) which is a desired product is obtained. The melting point of the obtained exemplary compound (1-37) is from 174° C. to 175° C. Further, the IR spectrum (infrared absorption spectrum) of the obtained exemplary compound (1-37) is shown in FIG. 5.

Synthesis Example 3

Synthesis of Exemplary Compound (1-11)

Figure 6:
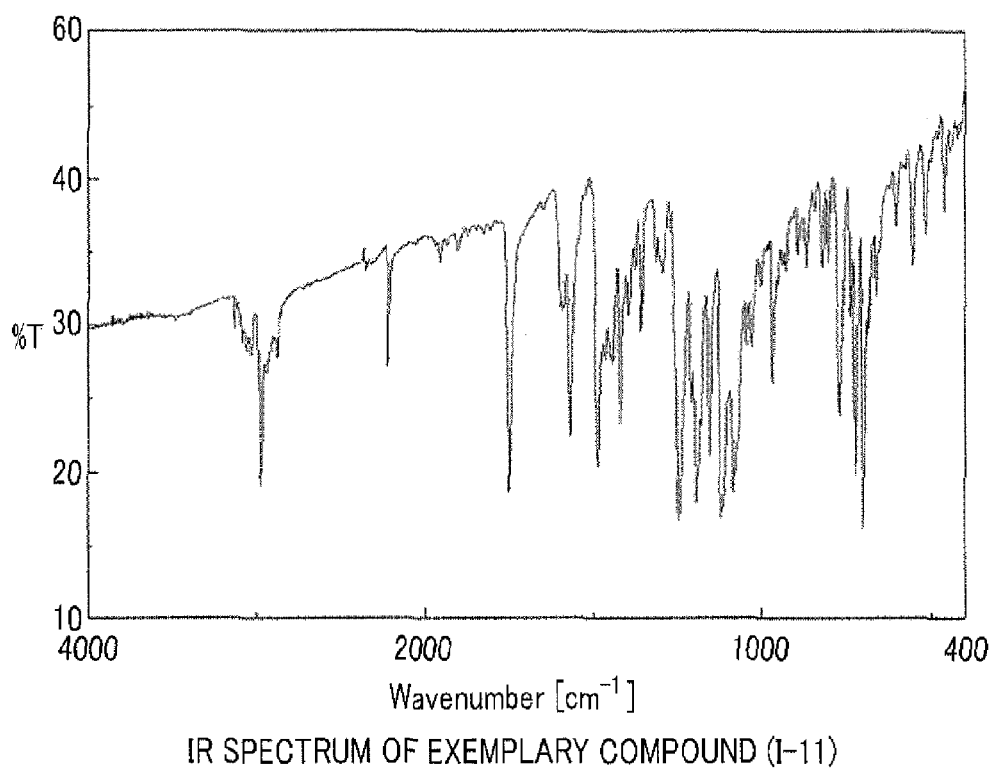
FIG. 6 is a graph showing an infrared absorption spectrum of an exemplary compound (1-11) obtained in Synthesis Example 3.

9.9 g of the exemplary compound (1-36) obtained in Synthesis Example 1 is dissolved in 150 ml of ethyl acetate under warming, and 2.3 g of malononitrile and 0.2 g of piperidine are added thereto, followed by stirring at 50° C. for 5 hours. The precipitated crystals are filtered and purified by silica gel chromatography to obtain 9.0 g of an exemplary compound (1-11) which is a desired product. The melting point of the obtained exemplary compound (1-11) is from 198° C. to 200° C. Further, the IR spectrum (infrared absorption spectrum) of the obtained exemplary compound (1-11) is shown in FIG. 6.

Synthesis Example 4

Synthesis of Exemplary Compound (1-12)

Figure 7:
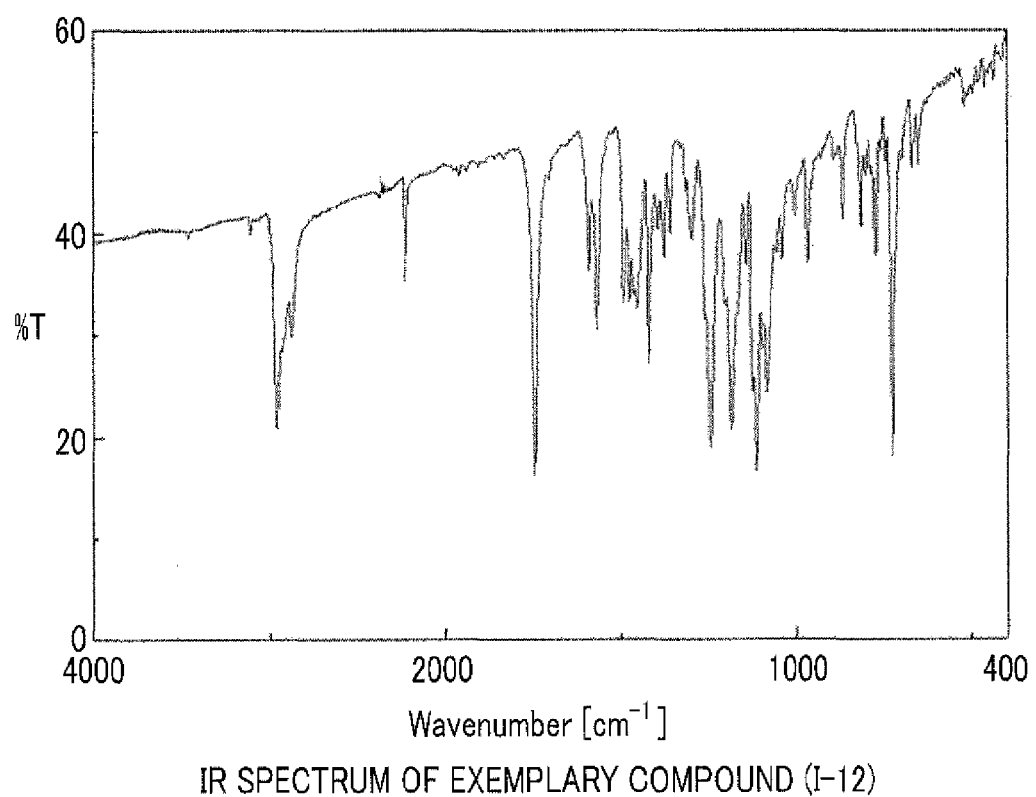
FIG. 7 is a graph showing an infrared absorption spectrum of an exemplary compound (1-12) obtained in Synthesis Example 4.

8.8 g of the exemplary compound (1-37) obtained in Synthesis Example 2 is dissolved in 150 ml of ethyl acetate under warming, and 2.3 g of malononitrile and 0.2 g of piperidine are added thereto, followed by stirring at 50° C. for 5 hours. The precipitated crystals are filtered and purified by silica gel chromatography to obtain 9.2 g of an exemplary compound (1-12) which is a desired product. The melting point of the obtained exemplary compound (1-12) is from 227° C. to 230° C. Further, the IR spectrum (infrared absorption spectrum) of the obtained exemplary compound (1-12) is shown in FIG. 7.

Comparative Synthesis Example 1

Synthesis of Comparative Compound 1 Shown Below

Figure 8:
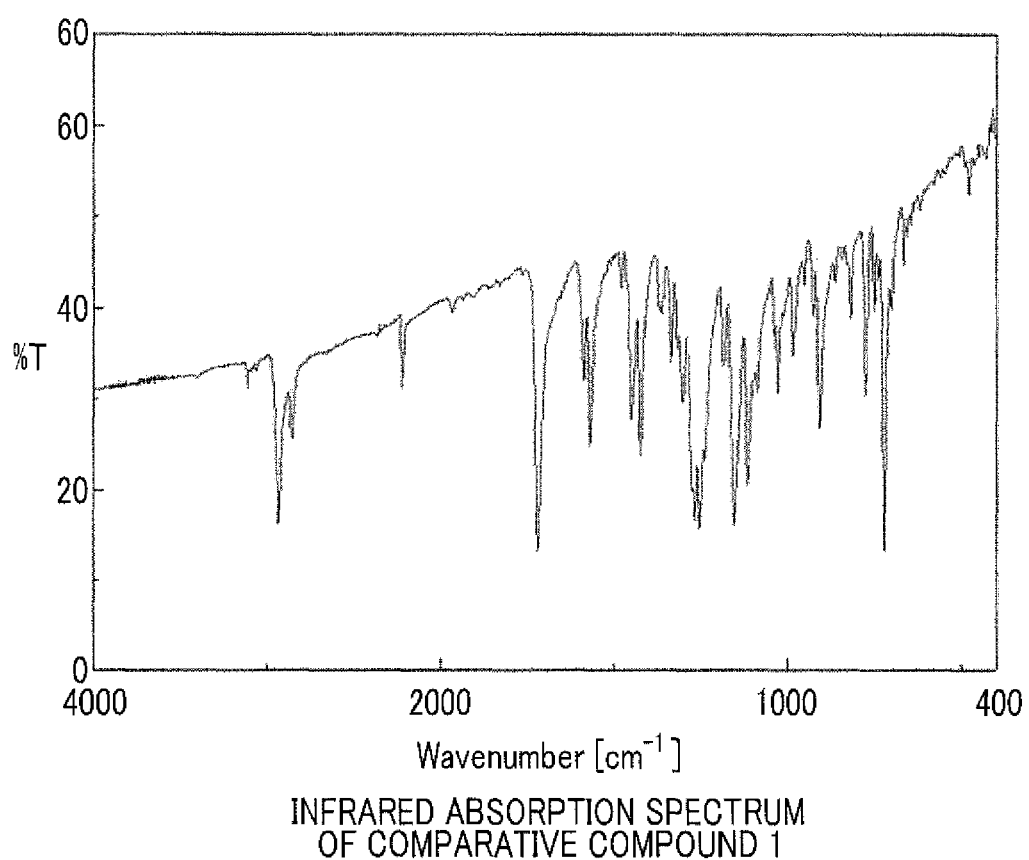
FIG. 8 is a graph showing an infrared absorption spectrum of a comparative compound 1 obtained in Comparative Synthesis Example 1.

By performing the synthesis in the same manner as in Synthesis Example 1 except that 2,4-di-t-pentylphenol of Synthesis Example 1 is changed to phenol, a comparative compound 1 is obtained. The melting point of the comparative compound 1 is from 198° C. to 199° C. Further, the IR spectrum (infrared absorption spectrum) of the obtained comparative compound 1 is shown in FIG. 8.

(Comparative compound 1)

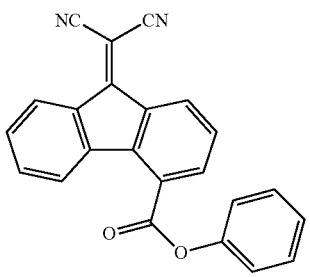

Comparative Synthesis Examples 2 to 5

Synthesis of Comparative Compounds 2 to 5 Shown Below

By performing the synthesis in the same manner as in Comparative Synthesis Example 1 except that phenol of Comparative Synthesis Example 1 is changed to each corresponding compound, comparative compounds 2 to 5 are obtained.

(Comparative compound 2)

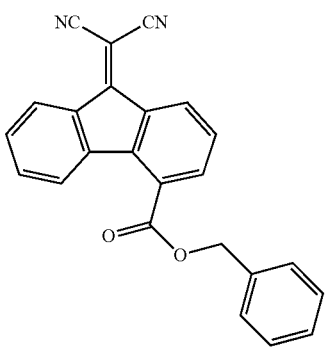

(Comparative compound 3)

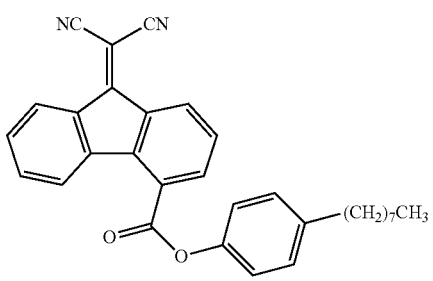

(Comparative compound 4)

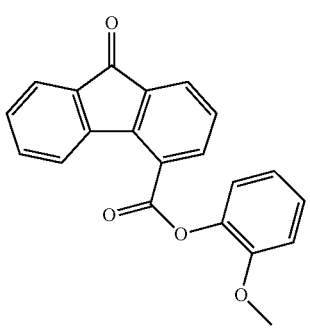

(Comparative compound 5)

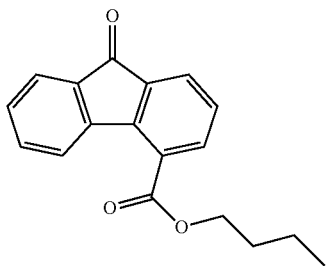

Preparation of Photoreceptor

Example 1

Formation of Undercoat Layer 100 parts by weight of zinc oxide (average particle diameter of 70 nm: manufactured by Tayca Corporation: specific surface area value of 15 m$^2$/g) is stirred and mixed with 500 parts by weight of tetrahydrofuran, and 1.2 parts by weight of a silane coupling agent (KBE502: manufactured by Shin-Etsu Chemical Co., Ltd.) is added thereto, followed by stirring for 2 hours. Thereafter, tetrahydrofuran is evaporated by distillation under reduced pressure, and baking is performed at 120° C. for 3 hours to obtain zinc oxide surface-treated with a silane coupling agent.

110 parts by weight of the obtained zinc oxide surface-treated with a silane coupling agent is stirred and mixed with 500 parts by weight of tetrahydrofuran, and a solution formed by dissolving 0.7 parts by weight of alizarin in 50 parts by weight of tetrahydrofuran is added thereto, followed by stirring at 50° C. for 4 hours. Subsequently, zinc oxide to which alizarin is attached is separated by filtration under a reduced pressure and dried under reduced pressure at 65° C. to obtain alizarin-attached zinc oxide.

38 parts by weight of a solution formed by dissolving 60 parts by weight of alizarin-attached zinc oxide, 13.5 parts by weight of a curing agent (blocked isocyanate, Sumidur 3175, manufactured by Sumitomo-Bayer Urethane Co., Ltd.) and 15 parts by weight of a butyral resin (S-Lec BM-1, manufactured by Sekisui Chemical Co., Ltd.) in 85 parts by weight of methyl ethyl ketone is mixed with 30 parts by weight of methyl ethyl ketone. The mixture is dispersed using a sand mill with glass beads having a diameter of 1 mmϕ for 2 hours and 30 minutes to obtain a dispersion.

0.005 part by weight of dioctyl tin dilaurate as a catalyst and 40 parts by weight of silicone resin particles (Tospearl 145, manufactured by GE Toshiba Silicone Co., Ltd.) are added to the obtained dispersion to obtain a coating liquid for forming an undercoat layer.

The obtained coating liquid is coated on an aluminum substrate having a diameter of 30 mm, a length of 340 mm, and a thickness of 1 mm by a dip coating method, and dried to cure at 170° C. for 35 minutes, thereby obtaining an undercoat layer having a thickness of 16 m.

Formation of Photosensitive layer

A mixture including 2 parts by weight of a hydroxygallium phthalocyanine pigment shown in Table 1 below as a charge generating material, 49 parts by weight of a copolymerization type polycarbonate resin (A) (viscosity average molecular weight of 50000) having the following structure as a binder resin, 200 parts by weight of tetrahydrofuran as a solvent, and 100 parts by weight of monochlorobenzene as a solvent is dispersed using a sand mill with glass beads having a diameter of 1 mmϕ for 3 hours to obtain a dispersion.

Polycarbonate resin (A)

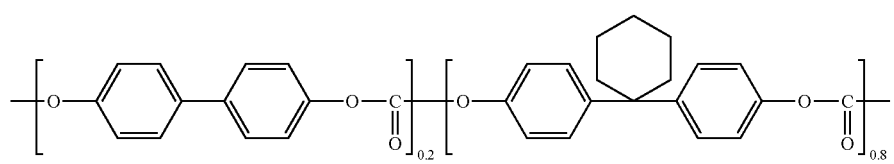

To the obtained dispersion are added 31 parts by weight of a hole transport material shown in Table 1 below and 15 parts by weight of an electron transport material shown in Table 1 and 0.001 parts by weight of a silicone oil KP340 (manufactured by Shin-Etsu Chemical Co., Ltd.), followed by stirring overnight, thereby obtaining a coating liquid for forming a photosensitive layer.

A single layer type photosensitive layer having a film thickness of 26 μm is formed by coating the obtained coating liquid for forming a photosensitive layer on the undercoat layer formed on the aluminum substrate using a dip coating method, and drying at 140° C. for 1 hour.

Through the above steps, an electrophotographic photoreceptor is prepared.

(HT-7)

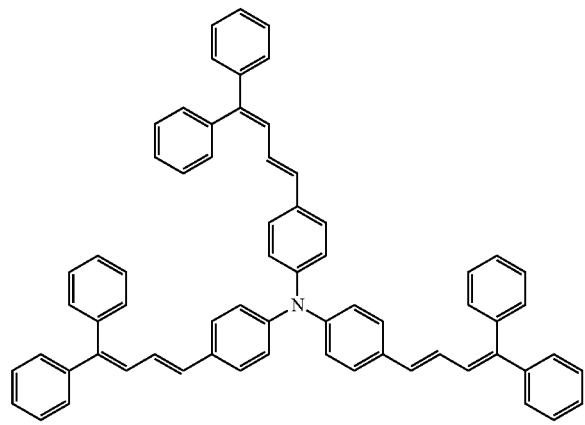

Examples 2 to 10 and Comparative Examples 1 to 5

In the same manner as in Example 1 except that the presence or absence of the undercoat layer, the kind of the charge generating material used in the coating liquid for forming a photosensitive layer, the kind of the hole transport material, and the kind of the electron transport material are changed according to Table 1, each electrophotographic photoreceptor is prepared.

TABLE 1

| Example | Photoreceptor | Undercoat layer | Charge generating material | Hole transport material | Electron transport material |
|---|---|---|---|---|---|
| Example 1 | Photoreceptor 1 | Included | HOGaPC | HT-7 | I-11 |
| Example 2 | Photoreceptor 2 | None | HOGaPC | HT-7 | I-11 |
| Example 3 | Photoreceptor 3 | Included | HOGaPC | HT-4 | I-12 |
| Example 4 | Photoreceptor 4 | None | HOGaPC | HT-4 | I-12 |
| Example 5 | Photoreceptor 5 | None | ClGaPC | HT-1 | I-11 |
| Example 6 | Photoreceptor 6 | None | ClGaPC | HT-1 | I-12 |
| Example 7 | Photoreceptor 7 | None | ClGaPC | HT-7 | I-12 |
| Example 8 | Photoreceptor 8 | None | ClGaPC | HT-7 | I-36 |
| Example 9 | Photoreceptor 9 | None | X type metal-free phthalocyanine | HT-1 | I-37 |
| Example 10 | Photoreceptor 10 | None | X type metal-free phthalocyanine | HT-1 | I-38 |
| Comparative Example 1 | Comparative photoreceptor 1 | Included | HOGaPC | HT-1 | Comparative compound 1 |
| Comparative Example 2 | Comparative photoreceptor 2 | None | HOGaPC | HT-1 | Comparative compound 2 |
| Comparative Example 3 | Comparative photoreceptor 3 | None | HOGaPC | HT-4 | Comparative compound 3 |
| Comparative Example 4 | Comparative photoreceptor 4 | None | ClGaPC | HT-1 | Comparative compound 4 |
| Comparative Example 5 | Comparative photoreceptor 5 | None | X type metal-free phthalocyanine | HT-1 | Comparative compound 5 |

Further, details on the abbreviations in Table 1 are as follows.

Charge Generating Material

HOGaPC: Hydroxygallium phthalocyanine (V type): V type hydroxygallium phthalocyanine pigment having diffraction peaks at the positions of at least 7.3°, 16.0°, 24.9°, and 28.0° by a Bragg angle (2θ±0.2°) in an X-ray diffraction spectrum obtained using CuKα characteristic X-ray (the maximum peak wavelength in a spectral absorption spectrum in a wavelength region of from 600 nm to 900 nm=820 nm, average particle diameter=0.12 μm, maximum particle diameter=0.2 μm, specific surface area value=60 $m^2/g$)

ClGaPC: Chlorogallium phthalocyanine: chlorogallium phthalocyanine pigment having diffraction peaks at the positions of at least 7.4°, 16.6°, 25.5°, and 28.3° by a Bragg angle (2θ±0.2°) in an X-ray diffraction spectrum obtained using CuKα characteristic X-ray (the maximum peak wavelength in a spectral absorption spectrum in a wavelength region of from 600 nm to 900 nm=780 nm, average particle diameter=0.15 μm, maximum particle diameter=0.2 μm, specific surface area value=56 $m^2/g$)

X type metal-free phthalocyanine: $H_2PC$: metal-free phthalocyanine pigment (phthalocyanine having two hydrogen atoms coordinated at the center of a phthalocyanine skeleton)

Hole Transport Material

HT-7: an exemplary compound (HT-7) of the compound represented by the formula (B-1)

HT-4: an exemplary compound (HT-4) of the compound represented by the formula (B-1)

HT-1: an exemplary compound (HT-1) of the compound represented by the formula (B-2)

Electron Transport Material 1-11: an exemplary compound (1-11) obtained in Synthesis Example 3

1-12: an exemplary compound (1-12) obtained in Synthesis Example 4

1-36: an exemplary compound (1-36) obtained in Synthesis Example 1

1-37: an exemplary compound (1-37) obtained in Synthesis Example 2

Comparative compound 1: Comparative compound 1 obtained in Comparative Synthesis Example 1

Comparative compound 2: Comparative compound 2 obtained in Comparative Synthesis Example 2

Comparative compound 3: Comparative compound 3 obtained in Comparative Synthesis Example 3

Comparative compound 4: Comparative compound 4 obtained in Comparative Synthesis Example 4

Comparative compound 5: Comparative compound 5 obtained in Comparative Synthesis Example 5

Evaluation

The following evaluations on each of the obtained electrophotographic photoreceptors are carried out, and the results are shown in Table 2.

Evaluation on Image Quality for Blur

Using Brother HL2270DW under an environment of a room temperature of 28° C. and a humidity of 85%, 5000 sheets of a 100% black solid image are formed and the presence or absence of generation of the blur of an image on the $5000^{th}$ sheet is visually observed and evaluated according to the following criteria.

A: No generation of blur (blur is not visually observed)

B: Some blur is visually observed in the transverse portion of a paper.

C: White blur is clearly generated

Evaluation of Charge Maintenance

Using Brother HL2270DW under an environment of a room temperature of 28° C. and a humidity of 85%, 20000 A4-sized sheets of a 100% black solid image are formed and the charge potentials are measured before and after forming 20000 sheets and the decrease in the charge potential by image formation is evaluated according to the following criteria.

Further, the charge potential is determined by measuring the potential of the surface of the electrophotographic photoreceptor before charging and exposing by a device in which a developer unit inside the HL2270DW is replaced by a potential probe.

A: The charge potential is decreased by 35 V or less.

B: The charge potential is decreased by more than 35 V and 50 V or less.

C: The charge potential is decreased by more than 50 V.

TABLE 2

| Example | Photoreceptor | Evaluation on blur | Initial charge potential | Charge potential after printing 20000 sheets | Evaluation on charge maintenance (decrease in potential) |
| --- | --- | --- | --- | --- | --- |
| Example 1 | Photoreceptor 1 | A | 600 V | 572 V | A (−28 V) |
| Example 2 | Photoreceptor 2 | A | 605 V | 578 V | A (−27 V) |
| Example 3 | Photoreceptor 3 | A | 601 V | 576 V | A (−25 V) |
| Example 4 | Photoreceptor 4 | A | 603 V | 571 V | A (−32 V) |
| Example 5 | Photoreceptor 5 | A | 596 V | 561 V | A (−35 V) |
| Example 6 | Photoreceptor 6 | A | 600 V | 572 V | A (−28 V) |
| Example 7 | Photoreceptor 7 | A | 602 V | 577 V | A (−25 V) |
| Example 8 | Photoreceptor 8 | A | 599 V | 578 V | A (−21 V) |
| Example 9 | Photoreceptor 9 | A | 606 V | 572 V | A (−34 V) |
| Example 10 | Photoreceptor 10 | A | 603 V | 570 V | A (−33 V) |
| Comparative Example 1 | Comparative photoreceptor 1 | C | 601 V | 543 V | C (−58 V) |
| Comparative Example 2 | Comparative photoreceptor 2 | C | 595 V | 541 V | C (−54 V) |
| Comparative Example 3 | Comparative photoreceptor 3 | B | 600 V | 557 V | B (−43 V) |
| Comparative Example 4 | Comparative photoreceptor 4 | B | 600 V | 553 V | B (−47 V) |

TABLE 2-continued

| Example | Photoreceptor | Evaluation on blur | Initial charge potential | Charge potential after printing 20000 sheets | Evaluation on charge maintenance (decrease in potential) |
|---|---|---|---|---|---|
| Comparative Example 5 | Comparative photoreceptor 5 | B | 604 V | 559 V | B (−45 V) |

Furthermore, as a result of evaluating the photoreceptors of Comparative Examples 1 and 2 as described above, it is found that slight crystallization is visually observed on the surface and defects in the form of dragged stripe patterns are found.

From the results above, it may be seen that in the present Example, the blur of an image hardly occurs and the charge maintenance is also good, as compared with Comparative Examples, and thus, the morphological change of the film is prevented and the stability is maintained.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An electron transport material represented by the following formula (1):

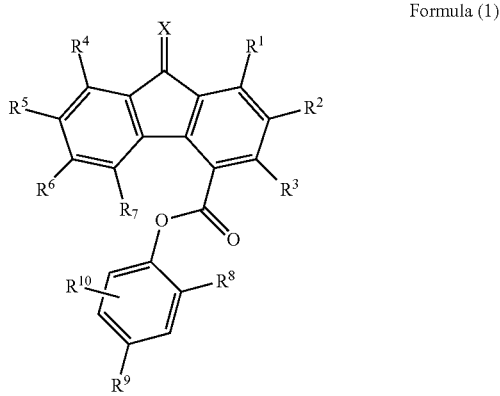

Formula (1)

wherein in the formula (1), X represents an oxygen atom or =C(CN)$_2$; $R^1$, $R^2$, $R^3$, $R^4$, $R^5$, $R^6$, and $R^7$ each independently represent a hydrogen atom, a halogen atom, a linear or branched alkyl group having 1 to 20 carbon atoms, an alkoxy group, an aryl group, or an aralkyl group; $R^8$, $R^9$, and $R^{10}$ each independently represent a hydrogen atom, a halogen atom, a linear or branched alkyl group having 1 to 20 carbon atoms, an aralkyl group, an aryl group, —$R^{11}$—O—$R^{12}$, or —$R^{13}$—CO—O—$R^{14}$; $R^{11}$ represents a linear or branched alkylene group having 1 to 10 carbon atoms; $R^{12}$ represents a linear or branched alkyl group having 1 to 10 carbon atoms; $R^{13}$ represents a single bond or a linear or branched alkylene group having 1 to 10 carbon atoms; and $R^{14}$ represents a linear or branched alkyl group having 1 to 10 carbon atoms, an aryl group, or an aralkyl group, provided that at least two or more groups of $R^8$, $R^9$, and $R^{10}$ represent a group other than a hydrogen atom.

2. The electron transport material according to claim 1, wherein at least one of $R^8$, $R^9$, and $R^{10}$ represents an organic group having 1 or more carbon atoms.

3. The electron transport material according to claim 2, wherein the organic group is a group selected from an alkyl group, an aralkyl group, an aryl group, —$R^{11}$—O—$R^{12}$ (in which $R^{11}$ is an alkylene group having 1 to 10 carbon atoms, and $R^{12}$ is an alkyl group having 1 to 10 carbon atoms), or —$R^{13}$—CO—O—$R^{14}$ (in which $R^{13}$ is a single bond or an alkylene group having 1 to 10 carbon atoms, and $R^{14}$ is a linear or branched alkyl group having 1 to 10 carbon atoms or an aralkyl group).

4. The electron transport material according to claim 1, wherein $R^1$, $R^2$, $R^3$, $R^4$, $R^5$, $R^6$, and $R^7$ each independently represent a hydrogen atom, a halogen atom, or a linear or branched alkyl group having 1 to 20 carbon atoms; $R^8$ and $R^9$ represent a linear or branched alkyl group having 1 to 10 carbon atoms or an aralkyl group and $R^{10}$ represents a hydrogen atom.

5. The electron transport material according to claim 1, wherein $R^1$, $R^2$, $R^3$, $R^4$, $R^5$, $R^6$, and $R^7$ each independently represent a hydrogen atom, a halogen atom, or an alkyl group having 1 to 10 carbon atoms; $R^8$ and $R^9$ both represent a branched alkyl group having 3 to 10 carbon atoms or an aralkyl group represented by —$R^{17}$—$Ar^{18}$ ($R^{17}$ represents a branched alkylene group having 3 to 10 carbon atoms, and $Ar^{18}$ represents an unsubstituted phenyl group); and $R^{10}$ represents a hydrogen atom.

6. An electrophotographic photoreceptor comprising a conductive substrate and a photosensitive layer including the electron transport material according to claim 1 provided on the conductive substrate.

7. A process cartridge comprising the electrophotographic photoreceptor according to claim 6, that is detachable from an image forming apparatus.

8. An image forming apparatus comprising:
the electrophotographic photoreceptor according to claim 6;
a charging unit that charges the surface of the electrophotographic photoreceptor;
an electrostatic latent image forming unit that forms an electrostatic latent image on the surface of a charged electrophotographic photoreceptor;
a developing unit that develops the electrostatic latent image formed on the surface of the electrophotographic photoreceptor by a developer containing a toner to form a toner image; and
a transfer unit that transfers the toner image to the surface of a recording medium.

* * * * *